United States Patent
Uchimura et al.

(10) Patent No.: US 11,213,776 B2
(45) Date of Patent: Jan. 4, 2022

(54) LEUKOCYTE REMOVAL FILTER MATERIAL AND LEUKOCYTE REMOVAL METHOD

(71) Applicant: ASAHI KASEI MEDICAL CO., LTD., Tokyo (JP)

(72) Inventors: Tetsuro Uchimura, Tokyo (JP); Nobukazu Shimada, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 489 days.

(21) Appl. No.: 15/103,435

(22) PCT Filed: Dec. 12, 2014

(86) PCT No.: PCT/JP2014/083023
§ 371 (c)(1),
(2) Date: Jun. 10, 2016

(87) PCT Pub. No.: WO2015/088019
PCT Pub. Date: Jun. 18, 2015

(65) Prior Publication Data
US 2016/0310883 A1 Oct. 27, 2016

(30) Foreign Application Priority Data
Dec. 13, 2013 (JP) .............................. JP2013-258525

(51) Int. Cl.
*B01D 39/16* (2006.01)
*D04H 1/56* (2006.01)
(Continued)

(52) U.S. Cl.
CPC ....... *B01D 39/1623* (2013.01); *A61M 1/3635* (2014.02); *B01D 39/163* (2013.01);
(Continued)

(58) Field of Classification Search
CPC ........ A61M 1/3635; A61M 2202/0439; A61M 2205/3368; B01D 2239/0492;
(Continued)

(56) References Cited

U.S. PATENT DOCUMENTS

| | | | |
|---|---|---|---|
| 4,701,267 A | 10/1987 | Watanabe et al. | |
| 5,407,581 A * | 4/1995 | Onodera | B01D 39/1623 210/321.69 |

(Continued)

FOREIGN PATENT DOCUMENTS

| | | |
|---|---|---|
| EP | 0491850 | 7/1998 |
| EP | 1582228 | 10/2005 |

(Continued)

OTHER PUBLICATIONS

International Search Report issued in PCT/JP2014/083023, dated Mar. 10, 2015.

(Continued)

*Primary Examiner* — Dirk R Bass
(74) *Attorney, Agent, or Firm* — Greenblum & Bernstein, P.L.C.

(57) ABSTRACT

There is disclosed a leukocyte removal filter material comprising a nonwoven fabric having polybutylene terephthalate fiber. The average fiber diameter of the nonwoven fabric is 0.9 to 1.5 μm, the formation index corresponding to a thickness of 0.3 mm of the nonwoven fabric is 15 to 70, and when the average fiber diameter of the nonwoven fabric is X and the specific surface area of the nonwoven fabric is Y, X and Y satisfy the following relational expression (1):

$$Y \geq -0.65 \times X + 1.75 \qquad (1).$$

15 Claims, 2 Drawing Sheets

(51) Int. Cl.
*B01J 20/26* (2006.01)
*D04H 1/435* (2012.01)
*A61M 1/36* (2006.01)
*B01J 20/28* (2006.01)

(52) U.S. Cl.
CPC .......... *B01J 20/261* (2013.01); *B01J 20/262* (2013.01); *B01J 20/28023* (2013.01); *B01J 20/28059* (2013.01); *D04H 1/435* (2013.01); *D04H 1/56* (2013.01); *A61M 2202/0439* (2013.01); *A61M 2205/3368* (2013.01); *B01D 2239/0492* (2013.01); *B01D 2239/0618* (2013.01); *B01D 2239/0622* (2013.01); *B01D 2239/10* (2013.01); *B01D 2239/1216* (2013.01); *B01D 2239/1233* (2013.01); *B01D 2239/1258* (2013.01)

(58) Field of Classification Search
CPC .... B01D 2239/0618; B01D 2239/0622; B01D 2239/10; B01D 2239/1216; B01D 2239/1233; B01D 2239/1258; B01D 39/1623; B01D 39/163; B01J 20/261; B01J 20/262; B01J 20/28023; B01J 20/28059; D04H 1/435; D04H 1/56
See application file for complete search history.

(56) References Cited

U.S. PATENT DOCUMENTS

| | | | |
|---|---|---|---|
| 5,580,465 A | 12/1996 | Pall et al. | |
| 6,977,044 B1* | 12/2005 | Oishi | A61M 1/3633 210/500.42 |
| 7,591,954 B2* | 9/2009 | Kimura | A61M 1/3496 210/488 |
| 2004/0104165 A1* | 6/2004 | Oishi | A61M 1/3633 210/490 |
| 2006/0016753 A1* | 1/2006 | Sowemimo-Coker | A61M 1/3633 210/651 |
| 2006/0184085 A1 | 8/2006 | Kimura et al. | |
| 2007/0199897 A1* | 8/2007 | Ozeki | A61M 1/3627 210/645 |
| 2007/0248942 A1* | 10/2007 | Onodera | B01D 15/00 435/2 |
| 2008/0011691 A1 | 1/2008 | Yamada et al. | |
| 2008/0110829 A1* | 5/2008 | Kobayashi | A61M 1/3633 210/645 |
| 2013/0192779 A1* | 8/2013 | Parker | C08G 63/6886 162/146 |
| 2013/0277297 A1* | 10/2013 | Suzuki | A61M 1/3633 210/257.1 |

FOREIGN PATENT DOCUMENTS

| | | |
|---|---|---|
| EP | 2633871 | 9/2013 |
| JP | 2-154051 | 6/1990 |
| JP | 2002-204910 | 7/2002 |
| JP | 2006-503670 | 2/2006 |
| JP | 2012-183237 | 9/2012 |
| WO | 2004/039474 | 5/2004 |
| WO | 2004/050146 | 6/2004 |
| WO | 2005/120600 | 12/2005 |
| WO | 2012/057029 | 5/2012 |

OTHER PUBLICATIONS

International Preliminary Report on Patentability issued in PCT/JP2014/083023, dated Jun. 23, 2016.

* cited by examiner

000000# LEUKOCYTE REMOVAL FILTER MATERIAL AND LEUKOCYTE REMOVAL METHOD

TECHNICAL FIELD

The present invention relates to a leukocyte removal filter material and a leukocyte removal method.

BACKGROUND ART

In the field of blood transfusion, so-called blood component transfusion of separating a blood component necessary for a recipient from a whole blood product and transfusing the blood component has generally been practiced in addition to so-called whole blood transfusion of transfusing a whole blood product in which blood collected from a donor is supplemented with an anticoagulant. The blood component transfusion includes red cell transfusion, platelet transfusion, plasma transfusion, and the like depending on the type of the blood component necessary for a recipient, and the blood product used for these transfusions includes a red cell product, a platelet product, a plasma product, and the like.

Furthermore, so-called leukocyte-free blood transfusion of transfusing a blood product after removing leukocytes contained in the blood product has become widespread recently. This is because it has been revealed that relatively slight adverse reactions accompanying blood transfusion, such as headache, nausea, chill, or febrile non-hemolytic reaction, and severe adverse reactions having serious effects on a recipient, such as alloantigen sensitization, viral infection, or post-transfusion GVHD, are mainly caused by leukocytes contained in the blood product used in blood transfusion. For preventing relatively slight adverse reactions such as headache, nausea, chill, or fever, it is considered necessary to remove leukocytes in the blood product until the residual rate becomes $10^{-1}$ to $10^{-2}$ or less. Also, for preventing alloantigen sensitization or viral infection, which is a severe adverse reaction, it is considered necessary to remove leukocytes until the residual rate becomes $10^{-4}$ to $10^{-6}$ or less.

Furthermore, in recent years, leukocyte removal therapy by the extracorporeal circulation of blood has been practiced in the treatment of diseases such as rheumatism or ulcerative colitis, and high clinical effects have been obtained.

Currently, methods of removing leukocytes from the blood product are roughly classified into two types: a centrifugation method of separating and removing leukocytes by using a centrifuge and utilizing the difference in specific gravity among blood components, and a filter method of removing leukocytes by using a filter material consisting of a fiber assembly such as a nonwoven fabric or a porous structure having continuous pores, or the like. The filter method which removes leukocytes by adhesion or adsorption is most widely used at present because of having the advantages that the operation is simple and the cost is low, for example.

In recent years, new demands for leukocyte removal filters have been proposed in the medical practice. One of the demands is to improve the recovery rate of useful components used as the blood product, such as plasma proteins. Although blood, which is a raw material for the blood product, is valuable blood that is covered by blood donation with good intentions in most cases, a problem is that plasma proteins and red cell products that have been adsorbed on a filter material in a leukocyte removal filter and thus become impossible to recover are disposed of together with the filter and end up in the garbage. Therefore, it is of significant importance to reduce the amount of the useful components adsorbed as compared with the current leukocyte removal filter and improve the recovery rate.

Thus, a leukocyte removal filter apparatus packed with a smaller amount of a filter material than ever by using a leukocyte removal filter material whose leukocyte removal performance per unit volume is high has been desired for satisfying the aforementioned demands in the medical practice. It is expected that the amount of blood remaining in the filter is decreased with decrease in the packing amount of the filter material so that the recovery rate of useful components can be improved over the conventional filter apparatus.

In the market, there has been a demand for the leukocyte removal filter to process a desired amount of blood in a short time. Therefore, the leukocyte removal filter apparatus is thought to have a shape in which the cross section is equal to or larger than that of the conventional apparatus and the thickness of the filter material is thinner. However, for decreasing the thickness of the filter material while maintaining the leukocyte removal performance, it is necessary to enhance the leukocyte removal performance per unit volume.

Meanwhile, the mechanism of leukocyte removal with a filter material such as a fiber assembly or a porous structure having continuous pores is considered to be based mainly on the adhesion or adsorption of leukocytes contacted with the filter material surface onto the filter material surface. Accordingly, in order to satisfy the aforementioned demands, studies to decrease the fiber diameter of the nonwoven fabric or increase the bulk density, for example, have been conducted as an approach for improvement in the leukocyte removal performance of the conventional filter material (see Patent Literatures 1 and 2).

Furthermore, a leukocyte removal method that attains high leukocyte removal performance and has a short processing time without causing clogging by using a leukocyte removal filter in which a specific structure in the thickness direction, i.e., the flow direction of liquids, is rendered uniform over the entire filtration surface of the nonwoven fabric has been proposed as another approach (see Patent Literature 3). In addition, a search for a filtering material suitable for the leukocyte removal filter material has been made so far (see Patent Literature 4).

CITATION LIST

Patent Literature

Patent Literature 1: Japanese Patent No. 1723513
Patent Literature 2: U.S. Pat. No. 5,580,465
Patent Literature 3: Japanese Patent No. 4134043
Patent Literature 4: European Patent No. 0491850

SUMMARY OF INVENTION

Technical Problem

However, for the filter material described in Patent Literature 1 or 2, the leukocyte removal performance can be improved by increasing the contact frequency with leukocytes, whereas pressure drop in allowing a blood product to pass therethrough is increased. Thus, a problem is that the processing speed is extremely decreased before completing the process of an expected amount of blood.

Furthermore, as for the leukocyte removal method described in Patent Literature 3, the present inventors have studied a nonwoven fabric used in the removal method, and consequently, the nonwoven fabric was suitable for improving the leukocyte removal performance over the conventional product, whereas the phenomenon was seen in which the processing speed was extremely decreased in the case of processing highly viscous blood. As the cause thereof, it is considered that the pore size configuration in the nonwoven fabric in the thickness direction was rendered uniform, whereby the liquid-flow resistance of blood per unit volume in the case of using the nonwoven fabric was increased so that clogging became more likely to occur during the processing of highly viscous blood. A method for uniformly controlling the pore size distribution/configuration of the nonwoven fabric is effective for the purpose of improving the leukocyte removal performance per unit volume. On the other hand, in the case of using a nonwoven fabric whose specific surface area is lower, since the number of pore size is decreased or the average pore size is reduced, the clogging of blood is thought to become much more likely to occur. Therefore, although it is presumed that the optimization of uniformity (=formation index) regarding a given range of a specific surface area is necessary, discussion has not been made in the invention described above.

Moreover, although a search for a filtering material suitable for the leukocyte removal filter material has been made as described in Patent Literature 4 above, the optimization of properties of the filter material, also including the control of the formation index, has not been performed.

In light of the problems of the conventional techniques described above and also in order to satisfy the new demands in the medical practice, an object of the present invention is to provide a leukocyte removal filter material and a leukocyte removal method capable of improving a recovery rate and a processing speed by suppressing the adsorption of useful components while possessing leukocyte removal performance equal to or higher than that of the conventional filter material.

Solution to Problem

The present inventors have conducted diligent studies by focusing on the difference in filtering material among nonwoven fabrics in order to achieve a shorter processing time (improvement in processing speed) while maintaining high leukocyte removal performance equivalent to that of the conventional product. As a result, it has been found that the processing time can be shortened (the processing speed can be improved) drastically as compared with the conventional filter material, and good performance balance can be exerted, by using polybutylene terephthalate as a filtering material of a nonwoven fabric while controlling the uniformity of the nonwoven fabric in a given range.

Specifically, the present invention relates to the following [1] to [14]:

[1] A leukocyte removal filter material comprising a nonwoven fabric having polybutylene terephthalate fiber, wherein
an average fiber diameter of the nonwoven fabric is 0.9 to 1.5 μm,
a formation index corresponding to a thickness of 0.3 mm of the nonwoven fabric is 15 to 70, and
when an average fiber diameter of the nonwoven fabric is X and a specific surface area of the nonwoven fabric is Y, X and Y satisfy the following relational expression (1):

$$Y \geq -0.65 \times X + 1.75 \tag{1}.$$

[2] The leukocyte removal filter material according to [1], wherein the nonwoven fabric is a nonwoven fabric obtained by a melt blown method.

[3] The leukocyte removal filter material according to [1] or [2], wherein an area shrinkage percentage when the nonwoven fabric is heat-treated at 115° C. for 240 minutes is 10% or less.

[4] The leukocyte removal filter material according to any one of [1] to [3], wherein a critical wetting surface tension of the nonwoven fabric is 50 dyn/cm or larger.

[5] The leukocyte removal filter material according to any one of [1] to [4], wherein a bulk density of the nonwoven fabric is 0.05 to 0.30 g/cm$^3$.

[6] The leukocyte removal filter material according to any one of [1] to [5], wherein a specific surface area of the nonwoven fabric is 0.8 to 3.2 m$^2$/g.

[7] The leukocyte removal filter material according to any one of [1] to [6], wherein an airflow resistance of the nonwoven fabric is 25 Pa·s·m/g or larger and 100 Pa·s·m/g or smaller.

[8] The leukocyte removal filter material according to any one of [1] to [7], wherein a peripheral surface portion of the nonwoven fabric has a nonionic group and a basic nitrogen-containing functional group, and a molar ratio of the nonionic group to the basic nitrogen-containing functional group is 20.0 to 50.0.

[9] The leukocyte removal filter material according to any one of [1] to [8], wherein when a specific surface area of the nonwoven fabric is Y and a formation index corresponding to a thickness of 0.3 mm of the nonwoven fabric is Z, Y and Z satisfy the following relational expression (2):

$$6.2 \leq Z/Y \leq 66 \tag{2}.$$

[10] The leukocyte removal filter material according to any one of [1] to [9], wherein when a mean flow pore size of the nonwoven fabric is W, W satisfies the following relational expression (3):

$$1.0 \leq W \leq 8.0 \tag{3}.$$

[11] The leukocyte removal filter material according to any one of [1] to [10], wherein when a whole blood product is allowed to pass through the filter material having an effective filtration area of 1.3 cm$^2$ and a mass of 320 g/m$^2$ at a flow rate of 1.2 mL/min, a leukocyte residual rate is 10.0×10$^{-3}$ or less, and a process pressure is 20.0 kPa or smaller.

[12] The leukocyte removal filter material according to any one of [1] to [11] for removing leukocytes from a leukocyte-containing solution which is any of whole blood, a concentrated red cell solution, platelet-rich plasma, and platelet-poor plasma.

[13] A method for removing leukocytes from a leukocyte-containing solution, comprising allowing the leukocyte-containing solution to pass through the leukocyte removal filter material according to any one of [1] to [11].

[14] The method according to [13], wherein the leukocyte-containing solution is any of whole blood, a concentrated red cell solution, platelet-rich plasma, and platelet-poor plasma.

Advantageous Effects of Invention

According to the present invention, it is possible to provide a leukocyte removal filter material and a leukocyte removal method capable of improving a recovery rate and a processing speed by suppressing the adsorption of useful components even while possessing leukocyte removal performance equal to or higher than that of the conventional filter material.

DESCRIPTION OF EMBODIMENTS

Hereinafter, a mode for carrying out the present invention (hereinafter, referred to as the present embodiment) will be described in detail. However, the present invention is not limited to the embodiment given below, and various changes or modifications can be made therein without departing from the gist of the present invention.

The leukocyte removal filter material of the present embodiment has a nonwoven fabric of polybutylene terephthalate. In other words, the leukocyte removal filter material of the present embodiment has a nonwoven fabric composed mainly of polybutylene terephthalate fiber. As for the nonwoven fabric, the average fiber diameter is 0.9 to 1.5 μm, and the formation index corresponding to a thickness of 0.3 mm is 15 to 70. When the average fiber diameter of the nonwoven fabric is X and the specific surface area is Y, X and Y satisfy the following relational expression (1):

$$Y \geq -0.65 \times X + 1.75 \qquad (1).$$

In the present specification, the "nonwoven fabric" includes a resin fiber formed by spinning a resin such as polybutylene terephthalate resin. This "nonwoven fabric" may be formed from only the resin fiber after spinning or may further have a coat layer formed on the outer peripheral surface of the resin fiber. Since the thickness of the coat layer is typically negligibly small as compared with the diameter of the resin fiber, the physical properties, such as average fiber diameter, formation index, and specific surface area, of the nonwoven fabric do not substantially vary between before and after the coat layer is formed, in most cases. That is, preferable aspects regarding the properties of the nonwoven fabric described below are applicable, regardless of the presence or absence of the coat layer.

Figure 1:
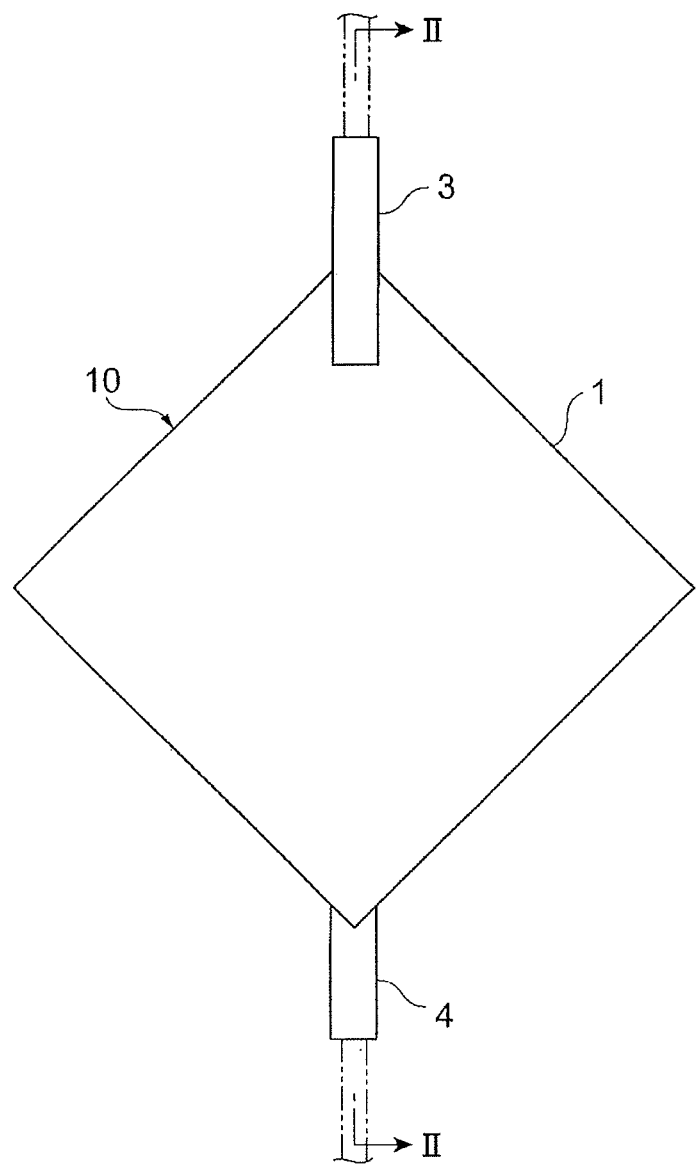
FIG. 1 is a schematic view of a leukocyte removal filter having a leukocyte removal filter material which is one embodiment of the present invention.

The leukocyte removal filter material of the present embodiment is housed in a container of a leukocyte removal filter and used for removing leukocytes from a leukocyte-containing solution. FIG. 1 is a schematic view of a leukocyte removal filter having the leukocyte removal filter material of the present embodiment, and FIG. 2 is a cross-sectional view taken along the II-II line of FIG. 1.

Figure 2:
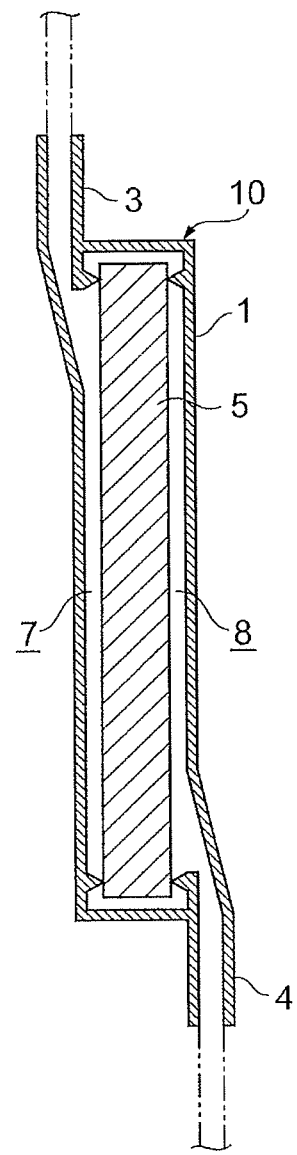
FIG. 2 is a cross-sectional view of the leukocyte removal filter having the leukocyte removal filter material which is one embodiment of the present invention.

As shown in FIGS. 1 and 2, a leukocyte removal filter 10 has a flat container 1 and a leukocyte removal filter material 5 which is housed in the inside thereof and is substantially in a dry state. The container 1 housing the leukocyte removal filter material 5 has a first port 3 disposed at the end on one principal surface side, and a second port 4 disposed at the end on another principal surface side. The space within the flat container 1 is partitioned by the leukocyte removal filter material 5 into space 7 on the first port side and space 8 on the second port side.

The leukocyte removal filter material 5 comprises a nonwoven fabric composed mainly of polybutylene terephthalate fiber (hereinafter, also referred to as a "polybutylene terephthalate nonwoven fabric"). The polybutylene terephthalate nonwoven fabric, as compared with, for example, a nonwoven fabric of polyethylene terephthalate fiber which is another polyester fiber, has equal or higher leukocyte removal performance, while the liquid-flow resistance of the nonwoven fabric per unit volume is low and thereby improving the processing speed. As a result, the performance balance is drastically improved. Furthermore, in the case of using polypropylene as a different filtering material, since the hydrophobicity of the nonwoven fabric is enhanced, the wettability for blood is reduced, and the effective filtration area is decreased. Thus, reduction in leukocyte removal performance as well as slowdown in processing speed due to one-side flow of blood or the like and further, hemolysis of red cells which are useful components, etc., become more likely to occur.

The reason why the performance balance of the polybutylene terephthalate is improved as compared with polyethylene terephthalate which is another polyester fiber can be explained as follows.

As for the polyester nonwoven fabric used as a leukocyte removal filter material, the stabilization of the physical properties by heat-treating the nonwoven fabric formed by spinning is often carried out. In this respect, the phenomenon in which the specific surface area is decreased by fiber fusion takes place. As a result, the leukocyte adsorption area is decreased, leading to reduction in leukocyte removal performance. In this context, the polybutylene terephthalate nonwoven fabric after spinning is highly crystalline as compared with the polyethylene terephthalate nonwoven fabric and therefore has a feature that the specific surface area is hardly decreased as compared with the polyethylene terephthalate nonwoven fabric after heat treatment.

In the case of using a nonwoven fabric as the leukocyte removal filter material, one of factors that largely influence the processing speed of blood and leukocyte removal performance includes an average fiber diameter. As the average fiber diameter is decreased, the mean flow pore size in the inside of the nonwoven fabric is decreased, and the clogging of blood cells consequently occurs so that the processing speed is slowed down. On the other hand, as the average fiber diameter is decreased, the specific surface area per unit weight is increased, and the effect of enhancing the leukocyte removal performance is therefore obtained.

In view of the above, when the polybutylene terephthalate nonwoven fabric is compared with the heat-treated polyethylene terephthalate nonwoven fabric having the same average fiber diameter, the specific surface area is high and therefore, the leukocyte removal performance is high, though the processing speed is equivalent. In other words, in the case of an equivalent specific surface area after heat treatment, the average fiber diameter of the polybutylene terephthalate nonwoven fabric can be set to be larger and therefore, the processing speed can be improved. That is, the performance balance can be explained to be improved according to the polybutylene terephthalate nonwoven fabric compared with the polyethylene terephthalate nonwoven fabric.

Particularly, in order to achieve good performance balance by using the polybutylene terephthalate nonwoven fabric, the average fiber diameter X and the specific surface area Y after heat treatment are controlled to satisfy the relational expression (1). In the expression (1), the value (1.75) of the Y intercept is preferably 1.95, more preferably 2.10, most preferably 2.30. In the case of the polyethylene terephthalate nonwoven fabric, even if the physical properties are controlled to satisfy the expression (1), it has been found that the process pressure is elevated during leukocyte removal, and the same performance as in the polybutylene terephthalate nonwoven fabric cannot be achieved.

Moreover, since the polybutylene terephthalate nonwoven fabric is highly crystalline as compared with, for example, a nonwoven fabric of polyethylene terephthalate which is another polyester fiber, the rebound intensity of the nonwoven fabric is increased, whereby the clamping between the container and the nonwoven fabric found in the case of using a leukocyte removal filter as described in Patent Literature 1 is strengthened so that the phenomenon in which blood goes out of the filter without passing through the nonwoven fabric (side leak phenomenon) becomes less likely to occur. As a result, there is the advantage of leading to improvement in leukocyte removal performance.

The formation index described in the present embodiment is a value obtained by irradiating the nonwoven fabric with light from the bottom, detecting the transmitted light with a charge-coupled device camera (hereinafter, abbreviated as a "CCD camera"), and multiplying the coefficient of variation (%) of the absorbance of the porous body (nonwoven fabric) detected by each pixel of the CCD camera by ten. A specific calculation method for the formation index is also described in the paragraphs [0016] to [0018] of Japanese Patent No. 4134043.

In the present embodiment, the formation index can be measured with, for example, a formation tester FMT-MIII (Nomura Shoji Co., Ltd.; manufactured in 2002; S/N: 130). The basic setting of the tester is not changed after the shipment from the factory, and the measurement can be carried out such that the total number of pixels of a CCD camera is, for example, approximately 3400. The measurement of the formation index can be carried out by adjusting the measurement size to 7 cm×3 cm (one pixel size=0.78 mm×0.78 mm) such that the total number of pixels is approximately 3400. However, the measurement size may be changed according to the shape of a sample such that the total number of pixels is equal. Since the formation index is largely influenced by the thickness, the formation index corresponding to a thickness of 0.3 mm can be calculated by the following method.

First, three nonwoven fabric sheets having a thickness of 0.3 mm or smaller are provided, and their respective formation indexes and thicknesses are measured. The thicknesses at four or more points are measured at a measurement pressure of 0.4 N by using, for example, a constant-pressure thickness meter (Ozaki Mfg. Co., Ltd., model FFA-12), and the average thereof can be defined as the thickness of the nonwoven fabric. Next, two of the three nonwoven fabric sheets measured are stacked such that the thickness is 0.3 mm or larger, and the formation index and the thickness are measured for the two nonwoven fabric sheets in a stacked state. After completing the formation index measurement for a total of three combinations, a linear regression equation of the thickness and the formation index is determined, and the formation index corresponding to a thickness of 0.3 mm can be calculated from the equation.

In the case where the thickness of the two nonwoven fabric sheets does not reach 0.3 mm, a plurality of nonwoven fabric sheets are stacked such that the thickness of the stack is 0.3 mm or larger, and the formation index is measured. Next, the number of nonwoven fabric sheets is decreased such that the thickness of the stack is 0.3 mm or smaller, and the formation index can be measured. The formation index is measured for all nonwoven fabric combinations in which the thickness of the stack is 0.3 mm or smaller. A linear regression equation of the thickness and the formation index is determined, and the formation index at a thickness of 0.3 mm can be determined from the equation.

Three or more nonwoven fabric sheets used in the formation index measurement are cut out of a single filter material, and they are typically nonwoven fabrics having substantially the same quality, i.e., nonwoven fabrics having the same physical properties (material, fiber diameter, bulk density, etc.). In the case where the number of nonwoven fabrics having substantially the same quality necessary for measurement cannot be obtained from a single filter material, the measurement may be carried out by combining nonwoven fabrics from the same type of filter material.

In the leukocyte removal method of the present embodiment, it is necessary to use a leukocyte removal filter comprising a nonwoven fabric whose formation index corresponding to a thickness of 0.3 mm is 15 or more and 70 or less. If the formation index is larger than 70, the structure in the thickness direction of the nonwoven fabric is non-uniform relative to the filtration surface direction, and blood does not flow evenly in the nonwoven fabric. Therefore, the leukocyte removal performance is reduced. On the other hand, if the formation index is smaller than 15, clogging becomes more likely to occur due to a rise in liquid-flow resistance, and the processing speed is slowed down. The formation index is more preferably 15 or more and 65 or less, further preferably 15 or more and 60 or less, particularly preferably 15 or more and 50 or less, most preferably 15 or more and 40 or less.

The leukocyte removal filter used in the leukocyte removal method of the present embodiment comprises a nonwoven fabric that exhibits the formation index described above, and such a highly uniform nonwoven fabric can be produced by any of a wet method and a dry method. In the present embodiment, particularly, production by a melt blowing method is preferable from the viewpoint of stably obtaining a nonwoven fabric whose formation index and average fiber diameter are optimal.

An example of the melt blowing method will be described as the method for producing the nonwoven fabric according to the present embodiment. A molten polymer fluid melted in an extruder is filtered through an appropriate filter, then introduced to a molten polymer inlet of a melt blowing die, and then discharged from an orifice nozzle. At the same time therewith, a heated gas introduced to a heated gas inlet is introduced to a heated gas ejection slit formed from the melt blowing die and a lip, and ejected therefrom so that the discharged molten polymer described above is attenuated to form ultrathin fibers. The formed ultrathin fibers are laminated to thereby obtain a nonwoven fabric. Examples of spinning factors to be studied in order to enhance the uniformity of the nonwoven fabric structure and to adjust the formation index to within the desired range include resin viscosity, a melting temperature, a discharging amount per single pore, a heated gas temperature, a heated gas pressure, and the distance between the spinning nozzle and the accumulation net. A nonwoven fabric that satisfies the formation index of the present embodiment can be obtained by optimizing these spinning factors. Particularly, for obtaining a nonwoven fabric whose formation index is lower, it is effective to set the distance between the spinning nozzle and the accumulation net to be short.

In the present embodiment, for example, polybutylene terephthalate resin having an intrinsic viscosity of 0.7 dl/g is heat-melted and discharged from the nozzle in a single pore discharging amount of 0.05 to 0.50 g/min, and air heated to 290 to 350° C. is ejected at a pressure of 0.03 to 3.0 kg/cm$^2$G from near the nozzle. Further, the formed ultrathin fibers are collected and deposited in a net conveyor located at a position 20 to 90 cm distant from the nozzle.

In this context, it is possible to obtain a nonwoven fabric having the targeted average fiber diameter (0.9 to 1.5 μm) by adjusting the temperature and pressure of the heated air. In this respect, the average fiber diameter of the nonwoven fabric tends to be thinner by increasing the air temperature and pressure.

It is also possible to control the formation index of the nonwoven fabric in the target range (15 to 70) by allowing the heated air used in spinning to be aspirated to the conveyor during the collection onto the conveyor, and adjusting the gas intake ability of a suction fan that aspirates and fixes the deposited nonwoven fabric so as not to blow off by the air. The gas intake ability of the fan is adjusted by the number of rotations of a motor used in the fan.

Heat treatment is often carried out after spinning for the purpose of stabilizing the physical properties of a polyester nonwoven fabric. In the present embodiment, a method of allowing the nonwoven fabric to stay in heated dry air, a method of allowing the nonwoven fabric to stay by dipping in hot water, a method of contacting the nonwoven fabric with a heated metal roll, or the like can be selected as a method for heat-treating the nonwoven fabric. In this respect, it is desirable to adjust the heating temperature and time according to the properties of the polymer so as to be able to apply a necessary and sufficient quantity of heat. For example, a sufficient quantity of heat can be applied by allowing the polybutylene terephthalate nonwoven fabric after spinning to stay in dry air of 140° C. for 120 seconds.

The average fiber diameter of the nonwoven fabric of the present embodiment is 0.9 μm or larger and 1.5 μm or smaller, preferably 1.0 μm or larger and 1.5 μm or smaller, further preferably 1.0 μm or larger and 1.4 μm or smaller. If the average fiber diameter is larger than 1.5 μm, there is a tendency that the number of contacts with leukocytes is decreased so that the capture of leukocytes becomes difficult. If the average fiber diameter is less than 0.9 μm, there is a tendency that clogging by blood cells is increased so that the processing speed is slowed down.

The average fiber diameter according to the present embodiment refers to a value determined according to the following procedures. Specifically, a portion of the filter material found to be substantially uniform is sampled at several points from one sheet of the nonwoven fabric constituting the filter material or a plurality of sheets of nonwoven fabrics having substantially the same quality, and photographs of the fibers in the sampled nonwoven fabrics are taken by using a scanning electron microscope. The photographs are continuously taken until the total number of photographed fibers to be measured exceeds 100. The diameters of all the fibers appearing in the photographs thus obtained are measured. In this context, the diameter refers to the width of the fiber in the direction perpendicular to the fiber axis. A value obtained by dividing the sum of the diameters of all the measured fibers by the number of fibers is defined as the average fiber diameter. However, when a plurality of fibers are overlapped and the width cannot be measured because a fiber is hidden behind another fiber, when a plurality of fibers are melted, for example, to form a thick fiber, when fibers significantly differing in diameter are mixed, when the boundary of the fibers is not clear because the focus of a photograph is incorrect, and the like, their data is omitted. Also when the average fiber diameter evidently differs between the upstream side and the downstream side, this is not considered as a single filter material. In this context, the phrase "average fiber diameter evidently differs" refers to the case where a significant difference is statistically observed. In this case, the upstream side and the downstream side are regarded as different filter materials, and their average fiber diameters are separately re-measured after distinguishing the interface therebetween.

The specific surface area described in the present embodiment is the surface area of the filter material (nonwoven fabric) per unit weight and can be measured by a BET adsorption method using, for example, Tristar 3000 apparatus manufactured by Micromeritics Japan and nitrogen as an adsorption gas. A larger specific surface area means that the area onto which cells and plasma proteins, etc., can be adsorbed is larger in processing blood by using a given weight of the filter material. It is preferable that the specific surface area of the nonwoven fabric according to the present embodiment is 0.8 $m^2/g$ or larger and 3.2 $m^2/g$ or smaller. If the specific surface area is larger than 3.2 $m^2/g$, there is a tendency that useful components such as plasma proteins are adsorbed onto the filter material during blood processing so that the recovery rate of the useful components is reduced. Also, if the specific surface area is smaller than 0.8 $m^2/g$, there is a tendency that the leukocyte removal performance is reduced as compared with the conventional filter material because the amount of leukocytes adsorbed is decreased. The specific surface area of the nonwoven fabric is more preferably 1.0 $m^2/g$ or larger and 3.2 $m^2/g$ or smaller, further preferably 1.1 $m^2/g$ or larger and 2.9 $m^2/g$ or smaller, particularly preferably 1.2 $m^2/g$ or larger and 2.9 $m^2/g$ or smaller, most preferably 1.2 $m^2/g$ or larger and 2.6 $m^2/g$ or smaller.

The airflow resistance of the nonwoven fabric of the present embodiment is a value measured as differential pressure generated when a given flow rate of air is allowed to flow in the filter material (nonwoven fabric), and is a value obtained by placing the filter material (nonwoven fabric) on a vent hole of an air permeability testing apparatus (e.g., manufactured by Kato Tech. Co., Ltd., KES-F8-AP1) and measuring pressure drop (Pa·s/m) generated when air is allowed to flow for approximately 10 seconds, and further dividing the pressure drop by the mass per unit area ($g/m^2$) of the filter material (nonwoven fabric). Here, the measurement is carried out five or more times while changing the cutout site, and the average value thereof is defined as the airflow resistance. Higher airflow resistance of the nonwoven fabric suggests that air is less likely to penetrate, and the fibers constituting the nonwoven fabric are entangled in a dense or uniform state, and means that the nonwoven fabric has the property of hindering a blood product from flowing. On the other hand, lower airflow resistance of the nonwoven fabric suggests that the fibers constituting the nonwoven fabric are entangled in a coarse or non-uniform state, and means that the nonwoven fabric has the property of facilitating the flow of a blood product. It is preferable that the airflow resistance of the nonwoven fabric of the present embodiment is 25 Pa·s·m/g or larger and 100 Pa·s·m/g or smaller, more preferably 30 Pa·s·m/g or larger and 90 Pa·s·m/g or smaller, further preferably 40 Pa·s·m/g or larger and 80 Pa·s·m/g or smaller. If the airflow resistance is smaller than 25 Pa·s·m/g, there is a tendency that the number of contacts with leukocytes is decreased so that the capture of leukocytes becomes difficult. If the airflow resistance of the nonwoven fabric is larger than 100 Pa·s·m/g, there is a tendency that clogging by blood cells is increased so that the processing speed is slowed down.

The mean flow pore size of the nonwoven fabric of the present embodiment can be measured in accordance with ASTM F316-86 by using Perm Porometer CFP-1200AEXS (automatic pore size distribution measurement system for porous materials) manufactured by Porous Materials, Inc. (PMI). In a nonwoven fabric whose mean flow pore size is large, a blood product flows easily, whereas the leukocyte removal performance is reduced. On the other hand, in a nonwoven fabric whose mean flow pore size is small, the leukocyte removal performance is improved, whereas a blood product is hindered from flowing, and the clogging of the nonwoven fabric also becomes more likely to occur.

In this context, the relationship between the formation index or the mean flow pore size and performance balance can be explained as follows.

The spatial arrangement of pore sizes formed between the fibers constituting the nonwoven fabric is rendered uniform by adjusting the formation index of the nonwoven fabric to be low. As a result, the pore size distribution becomes more sharp, and the mean flow pore size becomes smaller. That is, as mentioned above, the flow of blood becomes uniform relative to the filtration surface direction by lowering the formation index, whereby the leukocyte removal performance is improved. On the other hand, the mean flow pore size is accordingly reduced, whereby the processing speed is slowed down. Therefore, the proper adjustment of the formation index and the mean flow pore size is required for improving the performance balance.

Meanwhile, as mentioned above, improvement in performance balance is also possible by adjusting the average fiber diameter and optimizing the specific surface area and the mean flow pore size.

In conclusion, there is a tendency that the leukocyte removal performance is improved as the "formation index/specific surface area" becomes smaller, and the processing speed is improved as the mean flow pore size becomes larger. Thus, for achieving good performance balance, it is desirable that when the formation index of the nonwoven fabric is Z, the specific surface area of the nonwoven fabric is Y, and the mean flow pore size corresponding to a weight of 20 g/m² of the nonwoven fabric is W, Z, Y, and W satisfy the following relational expressions (2) and (3):

$$6.2 \leq Z/Y \ (g/m^2) \leq 66 \quad (2)$$

and $$1.0 \leq W \ (\mu m) \leq 8.0 \quad (3).$$

The optimization of the leukocyte removal performance is realized according to the relational expression (2). If Z/Y is larger than 66, there is a tendency that the leukocyte removal performance is reduced because the structure in the thickness direction of the nonwoven fabric is non-uniform relative to the filtration surface, and the blood cell adsorption area is also decreased. On the other hand, if Z/Y is smaller than 6.2, there is a tendency that clogging becomes more likely to occur so that the processing speed is slowed down. Z/Y is more preferably 8.0 g/m² or larger and 58 g/m² or smaller, further preferably 10 g/m² or larger and 50 g/m² or smaller, particularly preferably 12.5 g/m² or larger and 42 g/m² or smaller, most preferably 20 g/m² or larger and 33 g/m² or smaller.

The optimization of the processing speed can be realized according to the relational expression (3). If the mean flow pore size W is larger than 8.0 µm, there is a tendency that the number of contacts with leukocytes is decreased so that the capture of leukocytes becomes difficult. If the mean flow pore size W is less than 1.0 µm, there is a tendency that clogging by blood cells is increased so that the processing speed is slowed down. The mean flow pore size W is more preferably 1.5 µm or larger and 7.5 µm or smaller, further preferably 2.5 µm or larger and 7.0 µm or smaller, particularly preferably 3.5 µm or larger and 6.5 µm or smaller, most preferably 4.5 µm or larger and 6.5 µm or smaller.

It is preferable that the bulk density of the nonwoven fabric according to the present embodiment is 0.05 g/cm³ or larger and 0.30 g/cm³ or smaller, more preferably 0.07 g/cm³ or larger and 0.25 g/cm³ or smaller, particularly preferably 0.10 g/cm³ or larger and 0.22 g/cm³. If the bulk density is larger than 0.30 g/cm³, there is a tendency that the flow resistance of the nonwoven fabric is increased, and clogging by blood cells is accordingly increased so that the processing speed is slowed down. On the other hand, if the bulk density is smaller than 0.05 g/cm³, there is a tendency that the number of contacts with leukocytes is decreased so that the capture of leukocytes becomes difficult. Furthermore, the mechanical strength of the nonwoven fabric may be reduced.

It is also possible to specify the nonwoven fabric suitable for carrying out the present embodiment by means of a filling rate. The filling rate of the nonwoven fabric is calculated according to the following expression (10) by measuring the area, thickness, and weight of the nonwoven fabric cut into an arbitrary dimension and the specific gravity of the material constituting the nonwoven fabric:

Filling rate=[Weight (g) of the nonwoven fabric/(Area (cm²) of the nonwoven fabric×Thickness (cm) of the nonwoven fabric)]/Specific gravity (g/cm³) of the material constituting the nonwoven fabric (10).

It is preferable that the filling rate of the nonwoven fabric according to the present embodiment is 0.03 or more and 0.24 or less, more preferably 0.05 or more and 0.20 or less, particularly preferably 0.07 or more and 0.17 or less. If the filling rate is larger than 0.24, there is a tendency that the flow resistance of the nonwoven fabric is increased, and clogging by blood cells is accordingly increased so that the processing speed is slowed down. On the other hand, if the filling rate is smaller than 0.03, there is a tendency that the number of contacts with leukocytes is decreased so that the capture of leukocytes becomes difficult. Furthermore, the mechanical strength of the nonwoven fabric may be reduced.

The area shrinkage percentage of the nonwoven fabric according to the present embodiment is calculated according to the following expression (20) by accurately measuring the lateral and longitudinal size of the nonwoven fabric cut into approximately 20 cm×20 cm, then carrying out heat treatment at 115° C. for 240 minutes without fixing the nonwoven fabric with a pin or the like, and then measuring the lateral and longitudinal size again:

Area shrinkage percentage (%)=(Longitudinal length (cm) of the nonwoven fabric before the heat treatment×Lateral length (cm) of the nonwoven fabric before the heat treatment−Longitudinal length (cm) of the nonwoven fabric after the heat treatment×Lateral length (cm) of the nonwoven fabric after the heat treatment)/(Longitudinal length (cm) of the nonwoven fabric before the heat treatment×Lateral length (cm) of the nonwoven fabric before the heat treatment)×100 (20).

In the present embodiment, it is preferable that the area shrinkage percentage when the nonwoven fabric is subjected to heat treatment at 115° C. for 240 minutes is 10% or less, more preferably 3% or less, particularly preferably 2% or less, most preferably 1% or less. If the shrinkage percentage is larger than 10%, there is a tendency that not only is the pore size of the nonwoven fabric decreased in the case of carrying out severe temperature treatment such as high-temperature and high-pressure sterilization, but the pore size becomes non-uniform, whereby clogging by blood cells is increased so that the processing speed is slowed down. On the other hand, when the area shrinkage percentage is decreased to 10% or less, there is a tendency that the uniformity of the pore size is maintained even after sterilization treatment so that variation in processing speed can be prevented, and stable performance balance can be exerted, which is therefore preferable.

Particularly, since polybutylene terephthalate is highly crystalline as compared with, for example, a nonwoven fabric of polyethylene terephthalate which is another polyester fiber, the shrinkage in the planar direction is less likely to occur even under severe temperature history such as high-temperature and high-pressure sterilization. Thus, stable leukocyte removal performance and processing speed can be exerted, regardless of sterilization conditions.

It is preferable that the critical wetting surface tension (CWST) of the nonwoven fabric according to the present embodiment is 50 dyn/cm (0.0005 N/cm) or larger, more preferably 70 dyn/cm or larger, further preferably 85 dyn/cm or larger, particularly preferably 95 dyn/cm or larger. The nonwoven fabric having such a critical wetting surface tension secures stable wettability for blood and is thereby capable of efficiently performing leukocyte removal while suppressing clogging by a blood product.

In the present specification, CWST refers to a value determined according to the following method. Specifically, a plurality of aqueous solutions of sodium hydroxide, calcium chloride, sodium nitrate, acetic acid, and ethanol which differ in concentration such that the surface tension varies by 2 to 4 dyn/cm are prepared. The surface tension (dyn/cm (1 dyn/cm=$10^{-5}$ N/cm)) of each aqueous solution can be adjusted within the range of 94 to 115 for the aqueous sodium hydroxide solution, 90 to 94 for the aqueous calcium chloride solution, 75 to 87 for the aqueous sodium nitrate solution, 72.4 for pure water, 38 to 69 for the aqueous acetic acid solution, and 22 to 35 for the aqueous ethanol solution ("Kagaku Binran (Handbook of Chemistry in English), Basics II", revised 2nd edition, edited by The Chemical Society of Japan, Maruzen Publishing Co., Ltd., 1975, p. 164). Ten drops each of the thus-obtained aqueous solutions differing in surface tension by 2 to 4 dyn/cm are placed on a porous element (nonwoven fabric) in the ascending order of the surface tension, and left for 10 minutes. After the standing for 10 minutes, the case where nine or more drops out of the ten drops are absorbed by the porous element is defined as a wet state, and the case where such absorption is less than nine out of the ten drops is defined as a non-wet state. In this way, the liquids are assayed in the ascending order of the surface tension on the porous element, whereby the wet state and the non-wet state appear. In this respect, the average value of the surface tension value of a liquid observed as the wet state and the surface tension value of a liquid observed as the non-wet state are defined as the CWST value of the porous element. For example, the CWST value of a porous element that is wet by a liquid having a surface tension of 64 dyn/cm and is non-wet by a liquid having a surface tension of 66 dyn/cm is 65 dyn/cm.

In the present embodiment, the peripheral surface portion of the fiber constituting the nonwoven fabric may have a nonionic group and a basic nitrogen-containing functional group. For example, the polybutylene terephthalate fiber constituting the nonwoven fabric may have, at its surface portion, the nonionic group and the basic nitrogen-containing functional group, or the coat layer formed on the polybutylene terephthalate fiber may have, at its surface portion, the nonionic group and the basic nitrogen-containing functional group. The peripheral surface portion of the fiber constituting the nonwoven fabric refers to the surface portion of a coat layer in the case of coating the outer peripheral surface of the polybutylene terephthalate fiber with the coat layer containing a monomer and/or a polymer, and refers to the surface portion of spun polybutylene terephthalate fiber in the case of spinning a nonwoven fabric containing a nonionic group and a basic nitrogen-containing functional group and not forming the coat layer on the fiber.

It is preferable that the molar ratio of the nonionic group to the basic nitrogen-containing functional group is 20.0 to 50.0, more preferably 20.0 to 40.0, further preferably 30.0 to 40.0. The molar ratio of the nonionic group to the basic nitrogen-containing functional group can be measured by analysis such as NMR, IR, or TOF-SIMS. In this way, it is possible to secure stable wettability for blood and also to enhance, for example, the affinity of leukocytes for the nonwoven fabric, by specifying the contents of the basic nitrogen-containing functional group and the nonionic group. Thus, it is possible to efficiently carry out leukocyte removal while suppressing clogging by a blood product, for example.

Examples of the nonionic group include alkyl groups, alkoxy group, carbonyl groups, aldehyde groups, phenyl groups, amide groups, and hydroxyl groups. Examples of the basic nitrogen-containing functional group include amino groups represented by $-NH_2$, $-NR^2R^3$, or $-N^+R^4R^5R^6$ ($R^1$, $R^2$, $R^3$, $R^4$, $R^5$ and $R^6$ each represent an alkyl group having 1 to 3 carbon atoms).

The coat layer contains, for example, a copolymer having a monomer unit having the nonionic group and a monomer unit having the basic nitrogen-containing functional group. Examples of the monomer unit having the nonionic group include 2-hydroxyethyl (meth)acrylate, 2-hydroxypropyl (meth)acrylate, vinyl alcohol, (meth)acrylamide, and N-vinylpyrrolidone. Among these monomers, 2-hydroxyethyl (meth)acrylate is preferably used in view of easy availability, easy handleability during polymerization, performance when blood is allowed to flow, etc. The monomer unit of vinyl alcohol is usually formed by hydrolysis after polymerization of vinyl acetate.

Examples of the monomer unit having the basic nitrogen-containing functional group include: derivatives of (meth)acrylic acid such as diethylaminoethyl (meth)acrylate, dimethylaminoethyl (meth)acrylate, dimethylaminopropyl (meth)acrylate, and 3-dimethylamino-2-hydroxypropyl (meth)acrylate; styrene derivatives such as p-dimethylaminomethylstyrene and p-diethylaminoethylstyrene; vinyl derivatives of nitrogen-containing aromatic compounds such as 2-vinylpyridine, 4-vinylpyridine, and 4-vinylimidazole; and derivatives in which the vinyl compounds described above are converted to quaternary ammonium salts with alkyl halides or the like. Among these monomers, diethylaminoethyl (meth)acrylate and dimethylaminoethyl (meth)acrylate are preferably used in view of easy availability, easy handleability during polymerization, performance when blood is allowed to flow, etc.

The weight of the coat layer is, for example, about 1.0 to 40.0 mg with respect to 1 g of the weight of the nonwoven fabric (which typically corresponds to the total weight of the polybutylene terephthalate fiber and the coat layer).

The weight of the coat layer can be calculated by, for example, the following procedures. The nonwoven fabric before carrying the coat layer is dried for 1 hour in a dryer set to 60° C., and then left for 1 hour or longer in a desiccator, and then, the weight (A g) is measured. The nonwoven fabric carrying the coat layer is similarly dried for 1 hour in a dryer of 60° C. and then left for 1 hour or longer in a desiccator, and then, the weight (B g) is measured. The amount of the coat layer is calculated according to the following expression:

Weight (mg/g nonwoven fabric) of the coat layer= $(B-A) \times 1000/B$.

The coat layer containing the polymer (copolymer) can be formed by, for example, a method of dipping the nonwoven fabric in a polymer solution containing the polymer and a solvent, and then removing the solvent from the polymer solution attached to the nonwoven fabric.

In the leukocyte removal method of the present embodiment, the leukocyte removal filter is constituted by a leukocyte removal filter material having one sheet of a nonwoven fabric or a plurality of laminated nonwoven fabric layers, and a container having an inlet and an outlet for liquids and housing the leukocyte removal filter material. The nonwoven fabric used in the leukocyte removal method of the present embodiment may constitute the whole leukocyte removal filter material or may constitute a portion of the filter material. For example, a nonwoven fabric having a high formation index and/or a porous body having three-dimensional network continuous pores such as a sponge-like structure may be disposed on the upstream side, and a nonwoven fabric having a low formation index may be disposed on the downstream side:

The shape of this leukocyte removal filter material is not particularly limited, but may be, for example, a plate-like laminate or may be an article thereof molded in a cylindrical shape. The former one can be molded compactly and relatively conveniently and therefore has heretofore been widely used in blood transfusion filters or the like. The latter one is suitable for large-scale liquid processing and can therefore be preferably used as a filter for extracorporeal circulation.

The leukocyte removal filter material used in the present embodiment may be constituted by a single nonwoven fabric layer or may be constituted by a plurality of nonwoven fabric layers. In the case where the filter material is constituted by a plurality of nonwoven fabric layers, it is preferable that the filter material has a first nonwoven fabric layer which is disposed upstream and removes microaggregates, and a second nonwoven fabric layer which is disposed downstream of the first nonwoven fabric layer in order to remove leukocytes. For example, a nonwoven fabric layer consisting of a nonwoven fabric whose average fiber diameter is several to tens of μm is positioned on the inlet side as the first nonwoven fabric layer for aggregate removal. Next, a nonwoven fabric layer consisting of a nonwoven fabric whose average fiber diameter is 0.9 to 1.5 μm is positioned as the second nonwoven fabric layer for removing leukocytes. Further, a post nonwoven fabric layer may be disposed, if necessary, downstream of the second nonwoven fabric layer. The number of nonwoven fabric sheets forming each nonwoven fabric layer can be appropriately selected in consideration of leukocyte removal performance required for the leukocyte removal filter material, a processing time, or balance thereof, etc., and may be, for example, one sheet for each.

Particularly, it is preferable for a leukocyte removal filter having a plate-like and flexible container to be provided with the post nonwoven fabric layer, because it prevents the flow of blood from being inhibited in such a way that filter components are pressed against the outlet-side container due to positive pressure on the inlet side generated during filtration and further, and the outlet-side container is tightly contacted with the filter components due to negative pressure on the outlet side, and also because it enhances the weldability between the flexible container and the filter material. The post nonwoven fabric layer can employ a filtration medium known in the art, for example, a fibrous porous medium such as a nonwoven fabric, a woven fabric, or a mesh, and a porous body having three-dimensional network continuous pores. Examples of materials for these include polypropylene, polyethylene, styrene-isobutylene-styrene copolymers, polyurethane, and polyester. The case where the post nonwoven fabric layer is a nonwoven fabric is preferable from the viewpoint of productivity and the welding strength of the leukocyte removal filter. It is particularly preferable that the post nonwoven fabric layer has a plurality of protrusions by embossing or the like because the flow of blood is rendered more uniform.

The first and second nonwoven fabric layers may each be further constituted by plural types of nonwoven fabric layers, or only one of them may be constituted by plural types of nonwoven fabric layers. For example, a first nonwoven fabric layer consisting of a nonwoven fabric whose average fiber diameter is 30 to 40 μm and/or a nonwoven fabric whose average fiber diameter is 10 to 20 μm is positioned on the upstream side, and a second nonwoven fabric layer consisting of a nonwoven fabric whose average fiber diameter is 1.5 to 2.5 μm is positioned downstream of the first nonwoven fabric layer. Further, a third nonwoven fabric layer consisting of a nonwoven fabric whose average fiber diameter is 1.2 to 1.5 μm and/or 0.9 to 1.2 μm may be positioned and used. Alternatively, a nonwoven fabric having a thick average fiber diameter and a nonwoven fabric having a thin average fiber diameter may be alternately positioned. It is preferable that the nonwoven fabric having a thick fiber diameter is positioned on the upstream side from the viewpoint of improvement in flowability by cascade structure formation. As for other configurations, a third nonwoven fabric layer consisting of a nonwoven fabric whose formation index is 40 to 70 and/or 15 to 40 may be positioned and used as the third nonwoven fabric layer mentioned above. A nonwoven fabric having a high formation index and a nonwoven fabric having a low formation index may be alternately positioned. It is preferable that the nonwoven fabric having a high formation index is positioned on the upstream side.

Each nonwoven fabric layer constituting the leukocyte removal filter material may be modified at its surface by a technique known in the art such as coating, chemical treatment, or radiation treatment, for the purpose of controlling selective separation properties for blood cells, surface hydrophilicity, etc.

The material for the container housing the leukocyte removal filter material may be any of a rigid resin and a flexible resin. Examples of the rigid resin material include phenol resin, acrylic resin, epoxy resin, formaldehyde resin, urea resin, silicon resin, ABS resin, nylon, polyurethane, polycarbonate, vinyl chloride, polyethylene, polypropylene, polyester, and styrene-butadiene copolymers. The container of the flexible resin is preferably a sheeted or cylindrical molded product made of a flexible synthetic resin. The material is preferably one similar in thermal and electrical properties to the filter components, and examples of suitable materials include: thermoplastic elastomers such as soft polyvinyl chloride, polyurethane, ethylene-vinyl acetate copolymers, polyolefins such as polyethylene and polypropylene, hydrogenation products of styrene-butadiene-styrene copolymers, and styrene-isoprene-styrene copolymers or hydrogenation products thereof; and mixtures of the thermoplastic elastomers with softening agents such as polyolefins and ethylene-ethyl acrylate. Preferable materials for the container are soft vinyl chloride, polyurethane, ethylene-vinyl acetate copolymers, polyolefins, and thermoplastic elastomers composed mainly of these, more preferably soft vinyl chloride and polyolefins.

The shape of the container is not particularly limited as long as being a shape having an inlet for a leukocyte-containing solution and an outlet for a liquid from which leukocytes have been removed, but is preferably a shape adapted to the shape of the leukocyte removal filter material. In the case where the leukocyte removal filter material is, for example, plate-like, a flat shape consisting of a polygon such as a tetragon or a hexagon, or a curve such as a circle or an ellipse is acceptable. More specifically, as shown in FIG. 1 or 2, the container 1 preferably have a shape constituted by the space 7 having the first port 3 as a liquid inlet/outlet and the space 8 having the second port 4 as a liquid inlet/outlet, in which both of them sandwich the leukocyte removal filter material 5 either directly or via a support, whereby the inside of the filter is divided into two rooms to form the flat leukocyte removal filter 10. As another example, in the case where the leukocyte removal filter material is cylindrical, it is preferable that the container is also cylindrical. More specifically, the container preferably have a shape constituted by a tubular barrel housing the filter material, an inlet-side header having a liquid inlet, and an outlet-side header having a liquid outlet, in which the inside of the container is divided into two rooms by potting such that a liquid introduced from the inlet flows from the outer periphery to the inner periphery (or from the inner periphery to the outer periphery) of the cylindrical filter, to form the cylindrical leukocyte removal filter.

Next, the leukocyte removal method of the present embodiment will be described.

The leukocyte removal method of the present embodiment comprises allowing a leukocyte-containing solution to pass through a leukocyte removal filter having a leukocyte removal filter material comprising a nonwoven fabric housed in a container, to remove leukocytes from the leukocyte-containing solution. The nonwoven fabric according to the aforementioned embodiment containing polybutylene terephthalate fiber, wherein the average fiber diameter is 0.9 to 1.5 μm, and the formation index corresponding to a thickness of 0.3 mm is 15 to 70 is used as the nonwoven fabric.

The leukocyte-containing solution described in the present embodiment is a generic name for body fluids and synthetic blood containing leukocytes, and is specifically: whole blood and a liquid consisting of a single or plural types of blood components prepared from whole blood, such as whole blood, a concentrated red cell solution, a washed red cell suspension, a thawed red cell concentrate, synthetic blood, platelet-poor plasma (PPP), platelet-rich plasma (PRP), plasma, frozen plasma, a platelet concentrate, and buffy coat (BC); and a solution, a whole blood product, a red cell product, a platelet product, a plasma product, or the like in which the liquid is supplemented with an anticoagulant, a preservative solution, or the like. Here, a liquid obtained by treating the liquid mentioned above by the method of the present embodiment is referred to as a liquid from which leukocytes have been removed.

Hereinafter, one mode of a method for preparing each blood product by removing leukocytes by the leukocyte removal method will be described.

Preparation of Leukocyte-Free Whole Blood Product

The leukocyte-free whole blood product can be obtained by adding a preservative solution or an anticoagulant, such as citrate phosphate dextrose (CPD), citrate phosphate dextrose adenine-1 (CPDA-1), citrate phosphate-2-dextrose (CP2D), acid citrate dextrose formula-A (ACD-A), acid citrate dextrose formula-B (ACD-B), or heparin, to collected whole blood and removing leukocytes from the whole blood with the leukocyte removal filter.

In the preparation of the leukocyte-free whole blood product, in the case of leukocyte removal before preservation, the whole blood preserved at room temperature or under refrigeration can be subjected to leukocyte removal with the leukocyte removal filter at room temperature or under refrigeration preferably within 72 hours, more preferably within 24 hours, particularly preferably within 12 hours, most preferably within 8 hours after blood collection to thereby obtain the leukocyte-free whole blood product. In the case of leukocyte removal after preservation, leukocytes can be removed from the whole blood preserved at room temperature, under refrigeration, or under freezing, preferably within 24 hours before use, by using the leukocyte removal filter to thereby obtain the leukocyte-free whole blood product.

Preparation of Leukocyte-Free Red Cell Product

A preservative solution or an anticoagulant, such as CPD, CPDA-1, CP2D, CD-A, ACD-B, or heparin, is added to collected whole blood. A separation method for each blood component includes the case of carrying out centrifugation after removing leukocytes from the whole blood, and the case of removing leukocytes from red cells or red cells and BC after centrifuging the whole blood.

In the case of carrying out centrifugation after removing leukocytes from the whole blood, the leukocyte-free red cell product can be obtained by centrifuging the leukocyte-free whole blood.

In the case of centrifuging the whole blood before leukocyte removal, the centrifugation conditions include two types: soft spin conditions where it is separated into red cells and PRP, and hard spin conditions where it is separated into red cells, BC, and PPP. After addition of a preservative solution such as SAGM, AS-1, AS-3, AS-5, or MAP, if necessary, to red cells separated from the whole blood or red cells containing BC, leukocytes can be removed from the red cells with the leukocyte removal filter to thereby obtain the leukocyte-free red cell product.

In the preparation of the leukocyte-free red cell product, the whole blood preserved at room temperature or under refrigeration can be subjected to centrifugation preferably within 72 hours, more preferably within 48 hours, particularly preferably within 24 hours, most preferably within 12 hours after blood collection. In the case of leukocyte removal before preservation, leukocytes can be removed from the red cell product preserved at room temperature or under refrigeration, preferably within 120 hours, more preferably within 72 hours, particularly preferably within 24 hours, most preferably within 12 hours after blood collection, with the leukocyte removal filter at room temperature or under refrigeration to thereby obtain the leukocyte-free red cell product. In the case of leukocyte removal after preservation, leukocytes can be removed from the red cell product preserved at room temperature, under refrigeration, or under freezing, preferably within 24 hours before use, with the leukocyte removal filter to thereby obtain the leukocyte-free red cell product.

Preparation of Leukocyte-Free Platelet Product

A preservative solution or an anticoagulant, such as CPD, CPDA-1, CP2D, ACD-A, ACD-B, or heparin, is added to collected whole blood.

A separation method for each blood component includes the case of carrying out centrifugation after removing leukocytes from the whole blood, and the case of removing leukocytes from PRP or platelet after centrifuging the whole blood.

In the case of carrying out centrifugation after removing leukocytes from the whole blood, the leukocyte-free platelet product can be obtained by centrifuging the leukocyte-free whole blood.

In the case of centrifuging the whole blood before leukocyte removal, the centrifugation conditions include two types: soft spin conditions where it is separated into red cells and PRP, and hard spin conditions where it is separated into red cells, BC, and PPP. Under the soft spin conditions, leukocytes are removed from PRP separated from the whole blood with the leukocyte removal filter, and then, the leukocyte-free platelet product is obtained by centrifugation, or platelet and PPP are obtained by centrifuging PRP, and then, leukocytes can be removed with the leukocyte removal filter to obtain the leukocyte-free platelet product. Under the hard spin conditions, one unit or a pool of several to dozen units of BC separated from the whole blood is supplemented, if necessary, with a preservative solution, plasma, or the like, and subjected to centrifugation to thereby obtain platelet, and leukocytes can be removed from the obtained platelet with the leukocyte removal filter to thereby obtain the leukocyte-free platelet product.

In the preparation of the leukocyte-free platelet product, the whole blood preserved at room temperature is subjected to centrifugation preferably within 24 hours, more preferably within 12 hours, particularly preferably within 8 hours after blood collection. In the case of leukocyte removal before preservation, leukocytes can be removed from the platelet product preserved at room temperature, preferably within 120 hours, more preferably within 72 hours, particularly preferably within 24 hours, most preferably within 12 hours after blood collection, with the leukocyte removal filter at room temperature to thereby obtain the leukocyte-free platelet product. In the case of leukocyte removal after preservation, leukocytes can be removed from the platelet product preserved at room temperature, under refrigeration, or under freezing, preferably within 24 hours before use, with the leukocyte removal filter to thereby obtain the leukocyte-free platelet product.

Preparation of Leukocyte-Free Plasma Product

A preservative solution or an anticoagulant, such as CPD, CPDA-1, CP2D, ACD-A, ACD-B, or heparin, is added to collected whole blood.

A separation method for each blood component includes the case of carrying out centrifugation after removing leukocytes from the whole blood, and the case of removing leukocytes from PPP or PRP after centrifuging the whole blood.

In the case of carrying out centrifugation after removing leukocytes from the whole blood, the leukocyte-free plasma product can be obtained by centrifuging the leukocyte-free whole blood.

In the case of centrifuging the whole blood before leukocyte removal, the centrifugation conditions include two types: soft spin conditions where it is separated into red cells and PRP, and hard spin conditions where it is separated into red cells, BC, and PPP. Under the soft spin conditions, leukocytes are removed from PRP with the leukocyte removal filter, and then, the leukocyte-free plasma product is obtained by centrifugation, or PRP is centrifuged into PPP and platelet, and then, leukocytes can be removed with the leukocyte removal filter to obtain the leukocyte-free plasma product. Under the hard spin conditions, leukocytes can be removed from PPP with the leukocyte removal filter to thereby obtain the leukocyte-free plasma product.

In the preparation of the leukocyte-free plasma product, the whole blood preserved at room temperature or under refrigeration can be subjected to centrifugation preferably within 72 hours, more preferably within 48 hours, particularly preferably within 24 hours, most preferably within 12 hours after blood collection. Leukocytes can be removed from the plasma product preserved at room temperature or under refrigeration, preferably within 120 hours, more preferably within 72 hours, particularly preferably within 24 hours, most preferably within 12 hours after blood collection, with the leukocyte removal filter at room temperature or under refrigeration to thereby obtain the leukocyte-free plasma product. In the case of leukocyte removal after preservation, leukocytes can be removed from the plasma product preserved at room temperature, under refrigeration, or under freezing, preferably within 24 hours before use, with the leukocyte removal filter to thereby obtain the leukocyte-free plasma product.

Modes of from blood collection to the preparation of a leukocyte-free blood product may be any mode such as: a mode of collecting blood with a blood collection needle connected with a container for whole blood, and connecting the container containing whole blood or blood components after centrifugation with the leukocyte removal filter to carry out leukocyte removal; a mode of collecting blood using a circuit in which at least a blood collection needle, a blood container, and the leukocyte removal filter are sterilely connected, and carrying out leukocyte removal before centrifugation or after centrifugation; or a mode of connecting the leukocyte removal filter with a container containing blood components obtained with an automatic blood collection apparatus or using the leukocyte removal filter connected in advance with the container to carry out leukocyte removal, though the present embodiment is not limited by these modes. Alternatively, the leukocyte-free red cell product, the leukocyte-free platelet product, or the leukocyte-free plasma product may be obtained by centrifuging whole blood into each component in an automatic blood component collection apparatus, if necessary adding a preservative solution, and immediately thereafter allowing any of red cells, BC-containing red cells, BC, platelet, PRP, and PPP to pass through the leukocyte removal filter to remove leukocytes.

The present embodiment has higher leukocyte removal performance for all types of blood described above and has the effect of shortening the processing time without causing clogging, but is particularly suitable for red cell processing, in which the processing time of blood is prone to being extended.

In the preparation of these blood products, the leukocyte removal may be carried out by dropping leukocyte-containing blood from a container containing the leukocyte-containing liquid located at a position higher than the leukocyte removal filter to flow into the leukocyte removal filter via a tube, or may be carried out by allowing the leukocyte-containing blood to flow by increasing pressure from the inlet side of the leukocyte removal filter and/or reducing pressure from the outlet side of the leukocyte removal filter with means such as a pump.

Hereinafter, the leukocyte removal method using the leukocyte removal filter for extracorporeal circulation therapy will be described.

The inside of the leukocyte removal filter is primed with physiological saline or the like, which is then replaced with a solution containing at least an anticoagulant such as heparin, nafamostat mesilate, ACD-A, or ACD-B. While the anticoagulant is added to blood diverted outside the body, the blood is injected into the inlet of the leukocyte removal filter from a circuit connected with a human at a flow rate of 10 to 200 mL/min, and leukocytes can be removed with the leukocyte removal filter. In the initial period of leukocyte removal (amount processed: 0 to 0.5 L), flow rate of 10 to 50 mL/min is preferable, and 20 to 40 mL/min is more preferable. After the initial period of leukocyte removal (amount processed: 0.2 to 12 L), it is preferable to carry out processing at a flow rate of 30 to 120 mL/min, and a flow rate of 40 to 100 mL/min is more preferable, and a flow rate of 40 to 60 mL/min is particularly preferable. It is preferable to substitute the inside of the leukocyte removal filter with physiological saline or the like after the leukocyte removal to return the blood, because the blood within the leukocyte removal filter is not wasted.

EXAMPLES

Hereinafter, the present invention will be described with reference to Examples. However, the present invention is not intended to be limited by these.

Example 1

A nonwoven fabric consisting of polybutylene terephthalate (hereinafter, abbreviated as PBT) fiber and having a mass per unit area of 22 g/m$^2$, a thickness of 0.13 mm, a filling rate of 0.12, an average fiber diameter of 1.0 μm, and a formation index of 18.0 was used. The nonwoven fabric was prepared by a method of spinning polybutylene terephthalate by a melt blowing method to form a fiber assembly, and heat-treating the obtained fiber assembly at 140° C. for 120 seconds. The formation index of the nonwoven fabric was measured with a formation tester FMT-MIII (Nomura Shoji Co., Ltd.; manufactured in 2002; S/N: 130). The basic setting of the tester was not changed after the shipment from the factory, and the measurement was carried out such that the total number of pixels of a CCD camera was approximately 3400. The measurement of the formation index was carried out by setting the measurement size to 7 cm×3 cm (one pixel size=0.78 mm×0.78 mm) such that the total number of pixels was approximately 3400. Since the formation index is largely influenced by the thickness, the formation index corresponding to a thickness of 0.3 mm was calculated by the following method.

First, three nonwoven fabric sheets of 0.3 mm or smaller in thickness having substantially the same quality and a uniform thickness were provided, and their respective formation indexes and thicknesses were measured. The thicknesses at five points were measured at a measurement pressure of 0.4 N with a constant-pressure thickness meter (Ozaki Mfg. Co., Ltd., model FFA-12), and the average thereof was defined as the thickness of the nonwoven fabric. Next, two of the three nonwoven fabric sheets with their thicknesses measured were stacked such that the thickness was 0.3 mm or larger, and the formation index and the thickness of the stacked nonwoven fabric were measured. The formation index was measured for a total of three combinations of the two nonwoven fabric sheets. Then, a linear regression equation regarding the relationship between the thickness and the formation index was determined, and the formation index at a thickness of 0.3 mm was determined from the equation. In the case where the thickness of the two nonwoven fabric sheets did not reach 0.3 mm, a plurality of nonwoven fabric sheets were stacked such that the thickness of the stack was 0.3 mm or larger, and the formation index was measured. Next, the number of nonwoven fabric sheets was decreased such that the thickness of the stacked nonwoven fabric was 0.3 mm or smaller, and the formation index was measured. The formation index was measured for all nonwoven fabric combinations in which the thickness of the stacked nonwoven fabric was 0.3 mm or smaller. A linear regression equation regarding the relationship between the thickness and the formation index was determined, and the formation index at a thickness of 0.3 mm was determined from the equation.

Further, the nonwoven fabric was subjected to coating with a hydrophilic polymer by a method described below, and the nonwoven fabric having the coat layer formed by coating was used as a leukocyte removal filter material.

A copolymer of 2-hydroxyethyl methacrylate (hereinafter, abbreviated as HEMA) and diethylaminoethyl methacrylate (hereinafter, abbreviated as DEAMA) was synthesized by usual solution radical polymerization. The polymerization reaction was carried out at 60° C. for 8 hours in the presence of 1/200 mol of azoisobutyronitrile (AIBN) as an initiator at a monomer concentration of 1 mol/L in ethanol. The nonwoven fabric was dipped in the ethanol solution of the formed hydrophilic polymer. The absorbed redundant polymer solution was squeezed out of the nonwoven fabric took out from the polymer solution, and the polymer solution was dried off while dry air was sent, to form a coat layer covering the outer peripheral surface of the PBT fiber. The molar ratio of the nonionic group to the basic nitrogen-containing functional group at the peripheral surface portion (surface portion of the coat layer) of the nonwoven fabric after the polymer coating treatment was 32.3. The weight of the coat layer was 9.0 mg/g nonwoven fabric. The CWST value was 100 dyn/cm.

Next, a testing method to evaluate leukocyte removal performance will be described. The blood used in blood evaluation was whole blood, which was prepared by adding 14 mL of a CPD solution which was an anticoagulant to 100 mL of blood immediately after blood collection, mixing them, and leaving the mixture for 2 hours. Hereinafter, this blood prepared for blood evaluation is referred to as pre-filtration blood. A column having an effective filtration area of 1.3 cm$^2$ was packed with 16 nonwoven fabric sheets, and a syringe filled with the pre-filtration blood was connected with the inlet of the column through a tube made of polyvinyl chloride having an inside diameter of 3 mm and an outside diameter of 4.2 mm. Then, the pre-filtration blood was injected into the column at a flow rate of 1.2 mL/min with a syringe pump to recover 3 mL of the blood coming out of the outlet of the column (hereinafter, referred to as post-filtration blood). The leukocyte removal performance was evaluated by determining a leukocyte residual rate. The leukocyte residual rate was calculated according to the following expression (30) by measuring the number of leukocytes in the pre-filtration blood and the post-filtration blood by a flow cytometry method (apparatus: FACSCanto manufactured by Becton, Dickinson and Company):

Leukocyte residual rate=[Leukocyte concentration (number/μL) (post-filtration blood)]/[Leukocyte concentration (number/μL) (pre-filtration blood)]    (30).

The measurement of the number of leukocytes was carried out by sampling 100 μL of each blood and using Leucocount kit (BD (Becton, Dickinson and Company) Japan) containing beads.

Further, the blond process pressure was measured by the following method as a test item to evaluate the flowability of blood. A pressure gauge was connected with the tube connected with the inlet side of the column, and the pressure applied to the inlet side of the column at the completion of blood filtration was measured with the pressure gauge. The obtained value was defined as the blood process pressure.

The blood process pressure is used as an index for conveniently evaluating the processing speed in the case of performing gravity filtration with the leukocyte removal filter. It is known that as the blood process pressure is high, the processing speed of blood during the gravity filtration tends to be slow; and on the other hand, as the blood process pressure is low, the processing speed of blood during the gravity filtration tends to be fast.

It is practically desirable for the leukocyte removal filter material having a fast processing speed and efficiently removing leukocytes that the blood process pressure is 5.0 kPa or lower and the residual rate of leukocytes is $10.0 \times 10^{-3}$ or less.

As a result, the leukocyte residual rate was $0.3 \times 10^{-3}$, and the blood process pressure was 9.5 kPa, demonstrating a low blood process pressure and high leukocyte removal performance. The blood evaluation results of Examples 1 to 12 and Comparative Examples 1 to 28 were summarized in Tables 1 to 6.

The specific surface area and the mean flow pore size of the nonwoven fabric after heat treatment (before polymer coating treatment) are also shown in each table. The specific surface area was measured by a BET method. The mean flow pore size was measured in accordance with ASTM F316-86 by using Perm Porometer CFP-1200AEXS (automatic pore size distribution measurement system for porous materials) manufactured by Porous Materials, Inc. (PMI).

Example 2

A nonwoven fabric consisting of PBT fiber and having a mass per unit area of 23 g/m$^2$, a thickness of 0.13 mm, a filling rate of 0.13, an average fiber diameter of 1.0 µm, and a formation index of 68.9 was used. The nonwoven fabric was prepared by a method of subjecting a fiber assembly after spinning to heat treatment in the same way as in Example 1. The same polymer coating treatment as in Example 1 was carried out to form a coat layer covering the PBT fiber. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $7.1 \times 10^{-3}$, and the blood process pressure was 5.2 kPa, demonstrating a low blood process pressure and high leukocyte removal performance.

If the leukocyte residual rate becomes $10^{-4}$ or less, the number of residual leukocytes approaches the measurement limit. Thus results of preparing and testing the filter under such conditions that the leukocyte residual rate was $10^{-4}$ or more were shown in Examples described above. In actuality, a filter whose leukocyte residual rate is $10^{-4}$ to $10^{-6}$ or less, which is necessary for preventing severe adverse reactions, can be obtained by designing a filter suitable for the amount of a blood product to be processed by leukocyte removal.

Example 3

A nonwoven fabric consisting of PBT fiber and having a mass per unit area of 22 g/m$^2$, a thickness of 0.13 mm, a filling rate of 0.12, an average fiber diameter of 1.4 µm, and a formation index of 17.1 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $4.4 \times 10^{-3}$, and the blood process pressure was 7.3 kPa, demonstrating a low blood process pressure and high leukocyte removal performance.

Example 4

A nonwoven fabric consisting of PBT fiber and having a mass per unit area of 23 g/m$^2$, a thickness of 0.13 mm, a filling rate of 0.13, an average fiber diameter of 1.4 µm, and a formation index of 67.5 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $9.2 \times 10^{-3}$, and the blood process pressure was 3.0 kPa, demonstrating a low blood process pressure and high leukocyte removal performance.

Example 5

A nonwoven fabric consisting of PBT fiber and having a mass per unit area of 22 g/m$^2$, a thickness of 0.13 mm, a filling rate of 0.12, an average fiber diameter of 1.0 µm, and a formation index of 18.0 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $0.5 \times 10^{-3}$, and the blood process pressure was 8.4 kPa, demonstrating a low blood process pressure and high leukocyte removal performance.

Example 6

A nonwoven fabric consisting of PBT fiber and having a mass per unit area of 23 g/m$^2$, a thickness of 0.13 mm, a filling rate of 0.13, an average fiber diameter of 1.0 µm, and a formation index of 68.9 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducting the blood test by the same method as in Example 1, the leukocyte residual rate was $3.2 \times 10^{-3}$, and the blood process pressure was 4.7 kPa, demonstrating a low blood process pressure and high leukocyte removal performance.

Example 7

A nonwoven fabric consisting of PBT fiber and having a mass per unit area of 22 g/m², a thickness of 0.13 mm, a filling rate of 0.12, an average fiber diameter of 1.4 μm, and a formation index of 17.1 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducing the blood test by the same method as in Example 1, the leukocyte residual rate was $2.3 \times 10^{-3}$, and the blood process pressure was 6.8 kPa, demonstrating a low blood process pressure and high leukocyte removal performance.

Example 8

A nonwoven fabric consisting of PBT fiber and having a mass per unit area of 23 g/m², a thickness of 0.13 mm, a filling rate of 0.13, an average fiber diameter of 1.4 μm, and a formation index of 67.5 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducing the blood test by the same method as in Example 1, the leukocyte residual rate was $6.2 \times 10^{-3}$, and the blood process pressure was 2.7 kPa, demonstrating a low blood process pressure and high leukocyte removal performance.

Example 9

A nonwoven fabric consisting of PBT fiber and having a mass per unit area of 22 g/m², a thickness of 0.13 mm, a filling rate of 0.12, an average fiber diameter of 1.4 μm, and a formation index of 38.0 was used as a leukocyte removal filter material. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $2.7 \times 10^{-3}$, and the blood process pressure was 7.9 kPa, demonstrating a low blood process pressure and high leukocyte removal performance.

Example 10

A nonwoven fabric consisting of PBT fiber and having a mass per unit area of 23 g/m², a thickness of 0.13 mm, a filling rate of 0.13, an average fiber diameter of 1.3 μm, and a formation index of 55.0 was used as a leukocyte removal filter material. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $5.0 \times 10^{-3}$, and the blood process pressure was 6.6 kPa, demonstrating a low blood process pressure and high leukocyte removal performance.

Example 11

A nonwoven fabric consisting of PBT fiber and having a mass per unit area of 22 g/m², a thickness of 0.13 mm, a filling rate of 0.12, an average fiber diameter of 1.4 μm, and a formation index of 38.0 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducing the blood test by the same method as in Example 1, the leukocyte residual rate was $3.2 \times 10^{-3}$, and the blood process pressure was 7.2 kPa, demonstrating a low blood process pressure and high leukocyte removal performance.

Example 12

A nonwoven fabric consisting of PBT fiber and having a mass per unit area of 23 g/m², a thickness of 0.13 mm, a filling rate of 0.13, an average fiber diameter of 1.3 μm, and a formation index of 55.0 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducing the blood test by the same method as in Example 1, the leukocyte residual rate was $5.4 \times 10^{-3}$, and the blood process pressure was 5.8 kPa, demonstrating a low blood process pressure and high leukocyte removal performance.

Example 13

A nonwoven fabric consisting of PBT fiber and having a mass per unit area of 22 g/m², a thickness of 0.13 mm, a filling rate of 0.12, an average fiber diameter of 0.9 μm, and a formation index of 16.3 was used as a leukocyte removal filter material. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $0.2 \times 10^{-3}$, and the blood process pressure was 9.6 kPa, demonstrating a low blood process pressure and high leukocyte removal performance.

Example 14

A nonwoven fabric consisting of PBT fiber and having a mass per unit area of 23 g/m², a thickness of 0.13 mm, a filling rate of 0.13, an average fiber diameter of 1.5 μm, and a formation index of 65.1 was used as a leukocyte removal filter material. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $9.3 \times 10^{-3}$, and the blood process pressure was 3.2 kPa, demonstrating a low blood process pressure and high leukocyte removal performance.

Example 15

A nonwoven fabric consisting of PBT fiber and having a mass per unit area of 22 g/m$^2$, a thickness of 0.13 mm, a filling rate of 0.12, an average fiber diameter of 1.0 μm, and a formation index of 15.1 was used as a leukocyte removal filter material. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $0.1 \times 10^{-3}$, and the blood process pressure was 9.9 kPa, demonstrating a low blood process pressure and high leukocyte removal performance.

Example 16

A nonwoven fabric consisting of PBT fiber and having a mass per unit area of 22 g/m$^2$, a thickness of 0.13 mm, a filling rate of 0.12, an average fiber diameter of 0.9 μm, and a formation index of 1.6.3 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducing the blood test by the same method as in Example 1, the leukocyte residual rate was $0.3 \times 10^{-3}$, and the blood process pressure was 8.3 kPa, demonstrating a low blood process pressure and high leukocyte removal performance.

Example 17

A nonwoven fabric consisting of PBT fiber and having a mass per unit area of 23 g/m$^2$, a thickness of 0.13 mm, a filling rate of 0.13, an average fiber diameter of 1.5 μm, and a formation index of 65.1 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducing the blood test by the same method as in Example 1, the leukocyte residual rate was $9.7 \times 10^{-3}$, and the blood process pressure was 5.8 kPa, demonstrating a low blood process pressure and high leukocyte removal performance.

Example 18

A nonwoven fabric consisting of PBT fiber and having a mass per unit area of 22 g/m$^2$, a thickness of 0.13 mm, a filling rate of 0.12, an average fiber diameter of 1.0 μm, and a formation index of 15.1 was used as a leukocyte removal filter material. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducing the blood test by the same method as in Example 1, the leukocyte residual rate was $0.3 \times 10^{-3}$, and the blood process pressure was 9.7 kPa, demonstrating a low blood process pressure and high leukocyte removal performance.

Comparative Example 1

A nonwoven fabric consisting of polyethylene terephthalate (hereinafter, abbreviated as PET) fiber and having a mass per unit area of 22 g/m$^2$, a thickness of 0.13 mm, a filling rate of 0.12, an average fiber diameter of 1.0 μm, and a formation index of 17.0 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $0.6 \times 10^{-3}$, and the blood process pressure was 22.0 kPa. Although the leukocyte removal performance was high, the blood process pressure was high, demonstrating that this filter material is practically unsuitable.

Comparative Example 2

A nonwoven fabric consisting of PET fiber and having a mass per unit area of 23 g/m$^2$, a thickness of 0.13 mm, a filling rate of 0.13, an average fiber diameter of 1.0 μm, and a formation index of 68.1 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $21.2 \times 10^{-3}$, and the blood process pressure was 8.8 kPa. Although the blood process pressure was low, the leukocyte removal performance was low, demonstrating that this filter material is practically unsuitable.

Comparative Example 3

A nonwoven fabric consisting of PET fiber and having a mass per unit area of 22 g/m$^2$, a thickness of 0.13 mm, a filling rate of 0.12, an average fiber diameter of 1.4 µm, and a formation index of 16.6 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $4.8 \times 10^{-3}$, and the blood process pressure was 17.7 kPa. Although the leukocyte removal performance was high, the blood process pressure was high, demonstrating that this filter material is practically unsuitable.

Comparative Example 4

A nonwoven fabric consisting of PET fiber and having a mass per unit area of 23 g/m$^2$, a thickness of 0.13 mm, a filling rate of 0.13, an average fiber diameter of 1.4 µm, and a formation index of 67.7 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $48.9 \times 10^{-3}$, and the blood process pressure was 3.2 kPa. Although the blood process pressure was low, the leukocyte removal performance was low, demonstrating that this filter material is practically unsuitable.

Comparative Example 5

A nonwoven fabric consisting of PET fiber and having a mass per unit area of 22 g/m$^2$, a thickness of 0.13 mm, a filling rate of 0.12, an average fiber diameter of 1.0 µm, and a formation index of 17.0 was used. The nonwoven fabric was prepared by a method of subjecting a fiber assembly after spinning to heat treatment in the same way as in Example 1. The polymer coating treatment of the nonwoven fabric was not carried out. The CWST value was 71 dyn/cm. The nonwoven fabric without the polymer coating treatment described above was used as a filter material. As a result of conducting the blood test by the same method as in Example 1, the leukocyte residual rate was $1.0 \times 10^{-3}$, and the blood process pressure was 18.5 kPa. Although the leukocyte removal performance was high, the blood process pressure was high, demonstrating that this filter material is practically unsuitable.

Comparative Example 6

A nonwoven fabric consisting of PET fiber and having a mass per unit area of 23 g/m$^2$, a thickness of 0.13 mm, a filling rate of 0.13, an average fiber diameter of 1.0 µm, and a formation index of 68.1 was used. The nonwoven fabric was prepared by a method of subjecting a fiber assembly after spinning to heat treatment in the same way as in Example 1. The polymer coating treatment of the nonwoven fabric was not carried out. The CWST value was 71 dyn/cm. The nonwoven fabric without the polymer coating treatment described above was used as a filter material. As a result of conducting the blood test by the same method as in Example 1, the leukocyte residual rate was $27.3 \times 10^{-3}$, and the blood process pressure was 7.7 kPa. Although the blood process pressure was low, the leukocyte removal performance was low, demonstrating that this filter material is practically unsuitable.

Comparative Example 7

A nonwoven fabric consisting of PET fiber and having a mass per unit area of 22 g/m$^2$, a thickness of 0.13 mm, a filling rate of 0.12, an average fiber diameter of 1.4 µm, and a formation index of 16.6 was used. The nonwoven fabric was prepared by a method of subjecting a fiber assembly after spinning to heat treatment in the same way as in Example 1. The polymer coating treatment of the nonwoven fabric was not carried out. The CWST value was 71 dyn/cm. The nonwoven fabric without the polymer coating treatment was used as a filter material. As a result of conducting the blood test by the same method as in Example 1, the leukocyte residual rate was $6.5 \times 10^{-3}$, and the blood process pressure was 17.4 kPa. Although the leukocyte removal performance was high, the blood process pressure was high, demonstrating that this filter material is practically unsuitable.

Comparative Example 8

A nonwoven fabric consisting of PET fiber and having a mass per unit area of 23 g/m$^2$, a thickness of 0.13 mm, a filling rate of 0.13, an average fiber diameter of 1.4 µm, and a formation index of 67.7 was used. The nonwoven fabric was prepared by a method of subjecting a fiber assembly after spinning to heat treatment in the same way as in Example 1. The polymer coating treatment of the nonwoven fabric was not carried out. The CWST value was 71 dyn/cm. The nonwoven fabric without the polymer coating treatment described above was used as a filter material. As a result of conducting the blood test by the same method as in Example 1, the leukocyte residual rate was $57.3 \times 10^{-3}$, and the blood process pressure was 2.4 kPa. Although the blood process pressure was low, the leukocyte removal performance was low, demonstrating that this filter material is practically unsuitable.

Comparative Example 9

A nonwoven fabric consisting of PET fiber and having a mass per unit area of 22 g/m$^2$, a thickness of 0.13 mm, a filling rate of 0.12, an average fiber diameter of 1.4 µm, and a formation index of 38.0 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 1.00 dyn/cm. The nonwoven fabric after the polymer coating treatment was used as a leukocyte removal filter material. As a result of conducting the blood test by the same method as in Example 1, the leukocyte residual rate was $10.3 \times 10^{-3}$, and the blood process pressure was 5.1 kPa. Although the blood process pressure was low, the leukocyte removal performance was low, demonstrating that this filter material is practically unsuitable.

Comparative Example 10

A nonwoven fabric consisting of PET fiber and having a mass per unit area of 23 g/m$^2$, a thickness of 0.13 mm, a filling rate of 0.13, an average fiber diameter of 1.3 µm, and a formation index of 55.0 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $18.1 \times 10^{-3}$, and the blood process pressure was 6.4 kPa. Although the blood process pressure was low, the leukocyte removal performance was low, demonstrating that this filter material is practically unsuitable.

Comparative Example 11

A nonwoven fabric consisting of PET fiber and having a mass per unit area of 22 g/m$^2$, a thickness of 0.13 mm, a filling rate of 0.12, an average fiber diameter of 1.4 µm, and a formation index of 38.0 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $11.4 \times 10^{-3}$, and the blood process pressure was 4.7 kPa. Although the blood process pressure was low, the leukocyte removal performance was low, demonstrating that this filter material is practically unsuitable.

Comparative Example 12

A nonwoven fabric consisting of PET fiber and having a mass per unit area of 23 g/m$^2$, a thickness of 0.13 mm, a filling rate of 0.13, an average fiber diameter of 1.3 µm, and a formation index of 55.0 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $23.2 \times 10^{-3}$, and the blood process pressure was 6.1 kPa. Although the blood process pressure was low, the leukocyte removal performance was low, demonstrating that this filter material is practically unsuitable.

Comparative Example 13

A nonwoven fabric consisting of PET fiber and having a mass per unit area of 22 g/m$^2$, a thickness of 0.13 mm, a filling rate of 0.12, an average fiber diameter of 0.9 µm, and a formation index of 16.0 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $0.4 \times 10^{-3}$, and the blood process pressure was 24.1 kPa. Although the leukocyte removal performance was high, the blood process pressure was high, demonstrating that this filter material is practically unsuitable.

Comparative Example 14

A nonwoven fabric consisting of PET fiber and having a mass per unit area of 23 g/m$^2$, a thickness of 0.13 mm, a filling rate of 0.13, an average fiber diameter of 1.5 µm, and a formation index of 64.7 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $78.3 \times 10^{-3}$, and the blood process pressure was 1.9 kPa. Although the blood process pressure was low, the leukocyte removal performance was low, demonstrating that this filter material is practically unsuitable.

Comparative Example 15

A nonwoven fabric consisting of PET fiber and having a mass per unit area of 22 g/m$^2$, a thickness of 0.13 mm, a filling rate of 0.12, an average fiber diameter of 1.0 µm, and a formation index of 15.2 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $0.3 \times 10^{-3}$, and the blood process pressure was 29.3 kPa. Although the leukocyte removal performance was high, the blood process pressure was high, demonstrating that this filter material is practically unsuitable.

Comparative Example 16

A nonwoven fabric consisting of PET fiber and having a mass per unit area of 22 g/m$^2$, a thickness of 0.13 mm, a filling rate of 0.12, an average fiber diameter of 0.9 µm, and a formation index of 16.0 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducting the blood test by the same method as in Example 1, the leukocyte residual rate was $0.6 \times 10^{-3}$, and the blood process pressure was 22.1 kPa. Although the leukocyte removal performance was high, the blood process pressure was high, demonstrating that this filter material is practically unsuitable.

Comparative Example 17

A nonwoven fabric consisting of PET fiber and having a mass per unit area of 23 g/m$^2$, a thickness of 0.13 mm, a filling rate of 0.13, an average fiber diameter of 1.5 µm, and a formation index of 64.7 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $81.4 \times 10^{-3}$, and the blood process pressure was 1.8 kPa. Although the blood process pressure was low, the leukocyte removal performance was low, demonstrating that this filter material is practically unsuitable.

Comparative Example 18

A nonwoven fabric consisting of PET fiber and having a mass per unit area of 22 g/m$^2$, a thickness of 0.13 mm, a filling rate of 0.12, an average fiber diameter of 1.0 µm, and a formation index of 15.2 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $0.5 \times 10^{-3}$, and the blood process pressure was 27.9 kPa. Although the leukocyte removal performance was high, the blood process pressure was high, demonstrating that this filter material is practically unsuitable.

Comparative Example 19

A nonwoven fabric consisting of PBT fiber and having a mass per unit area of 22 g/m$^2$, a thickness of 0.13 mm, a filling rate of 0.12, an average fiber diameter of 0.8 µm, and a formation index of 16.1 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $0.7 \times 10^{-3}$, and the blood process pressure was 43.0 kPa. Although the leukocyte removal performance was high, the blood process pressure was high, demonstrating that this filter material is practically unsuitable.

Comparative Example 20

A nonwoven fabric consisting of PBT fiber and having a mass per unit area of 22 g/m$^2$, a thickness of 0.13 mm, a filling rate of 0.12, an average fiber diameter of 1.6 µm, and a formation index of 66.1 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $19.3 \times 10^{-3}$, and the blood process pressure was 2.7 kPa. Although the blood process pressure was low, the leukocyte removal performance was low, demonstrating that this filter material is practically unsuitable.

Comparative Example 21

A nonwoven fabric consisting of PBT fiber and having a mass per unit area of 22 g/m$^2$, a thickness of 0.13 mm, a filling rate of 0.12, an average fiber diameter of 1.0 µm, and a formation index of 13.5 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $1.3 \times 10^{-3}$, and the blood process pressure was 20.1 kPa. Although the leukocyte removal performance was high, the blood process pressure was high, demonstrating that this filter material is practically unsuitable.

Comparative Example 22

A nonwoven fabric consisting of PBT fiber and having a mass per unit area of 22 g/m$^2$, a thickness of 0.13 mm, a filling rate of 0.12, an average fiber diameter of 1.4 µm, and a formation index of 71.5 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $28.5 \times 10^{-3}$, and the blood process pressure was 4.3 kPa. Although the blood process pressure was low, the leukocyte removal performance was low, demonstrating that this filter material is practically unsuitable.

Comparative Example 23

A nonwoven fabric consisting of PBT fiber and having a mass per unit area of 22 g/m$^2$, a thickness of 0.13 mm, a filling rate of 0.12, an average fiber diameter of 0.8 µm, and a formation index of 16.1 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material; As a result of conducting the blood test by the same method as in Example 1, the leukocyte residual rate was $1.2 \times 10^{-3}$, and the blood process pressure was 39.0 kPa. Although the leukocyte removal performance was high, the blood process pressure was high, demonstrating that this filter material is practically unsuitable.

Comparative Example 24

A nonwoven fabric consisting of PBT fiber and having a mass per unit area of 22 g/m$^2$, a thickness of 0.13 mm, a filling rate of 0.12, an average fiber diameter of 1.6 μm, and a formation index of 66.1 was used. The nonwoven fabric was prepared by a method of subjecting a fiber assembly after spinning to heat treatment in the same way as in Example 1. The polymer coating treatment of the nonwoven fabric was not carried out. The CYST value was 51 dyn/cm. The nonwoven fabric without the polymer coating treatment described above was used as a filter material. As a result of conducting the blood test by the same method as in Example 1, the leukocyte residual rate was $24.0 \times 10^{-3}$, and the blood process pressure was 2.2 kPa. Although the blood process pressure was low, the leukocyte removal performance was low, demonstrating that this filter material is practically unsuitable.

Comparative Example 25

A nonwoven fabric consisting of PBT fiber and having a mass per unit area of 22 g/m$^2$, a thickness of 0.13 mm, a filling rate of 0.12, an average fiber diameter of 1.0 μm, and a formation index of 13.5 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $4.2 \times 10^{-3}$, and the blood process pressure was 15.0 kPa. Although the leukocyte removal performance was high, the blood process pressure was high, demonstrating that this filter material is practically unsuitable.

Comparative Example 26

A nonwoven fabric consisting of PBT fiber and having a mass per unit area of 22 g/m$^2$, a thickness of 0.13 mm, a filling rate of 0.12, an average fiber diameter of 1.4 μm, and a formation index of 71.5 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $31.0 \times 10^{-3}$, and the blood process pressure was 3.5 kPa. Although the blood process pressure was low, the leukocyte removal performance was low, demonstrating that this filter material is practically unsuitable.

Comparative Example 27

A nonwoven fabric consisting of PBT fiber and having a mass per unit area of 22 g/m$^2$, a thickness of 0.13 mm, a filling rate of 0.12, an average fiber diameter of 1.0 μm, and a formation index of 71.3 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $18.4 \times 10^{-3}$, and the blood process pressure was 4.4 kPa. Although the blood process pressure was low, the leukocyte removal performance was low, demonstrating that this filter material is practically unsuitable.

Comparative Example 28

A nonwoven fabric consisting of PBT fiber and having a mass per unit area of 22 g/m$^2$, a thickness of 0.13 mm, a filling rate of 0.12, an average fiber diameter of 0.8 μm, and a formation index of 67.3 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $11.3 \times 10^{-3}$, and the blood process pressure was 10.9 kPa. Although the leukocyte removal performance was high, the blood process pressure was high, demonstrating that this filter material is practically unsuitable.

Comparative Example 29

A nonwoven fabric consisting of PBT fiber and having a mass per unit area of 22 g/m$^2$, a thickness of 0.13 mm, a filling rate of 0.12, an average fiber diameter of 1.4 μm, and a formation index of 13.5 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $2.8 \times 10^{-3}$, and the blood process pressure was 15.1 kPa. Although the leukocyte removal performance was high, the blood process pressure was high, demonstrating that this filter material is practically unsuitable.

Comparative Example 30

A nonwoven fabric consisting of PBT fiber and having a mass per unit area of 22 g/m$^2$, a thickness of 0.13 mm, a filling rate of 0.12, an average fiber diameter of 1.6 μm, and a formation index of 15.9 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $10.1 \times 10^{-3}$, and the blood process pressure was 4.9 kPa. Although the blood process pressure was low, the leukocyte removal performance was low, demonstrating that this filter material is practically unsuitable.

Comparative Example 31

A nonwoven fabric consisting of PBT fiber and having a mass per unit area of 22 g/m$^2$, a thickness of 0.13 mm, a filling rate of 0.12, an average fiber diameter of 1.0 µm, and a formation index of 70.8 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment was used as a filter material. As a result of conducing the blood test by the same method as in Example 1, the leukocyte residual rate was $19.7 \times 10^{-3}$, and the blood process pressure was 3.9 kPa. Although the blood process pressure was low, the leukocyte removal performance was low, demonstrating that this filter material is practically unsuitable.

Comparative Example 32

A nonwoven fabric consisting of PBT fiber and having a mass per unit area of 22 g/m$^2$, a thickness of 0.13 mm, a filling rate of 0.12, an average fiber diameter of 0.8 µm, and a formation index of 68.9 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducing the blood test by the same method as in Example 1, the leukocyte residual rate was $12.3 \times 10^{-3}$, and the blood process pressure was 10.2 kPa. The leukocyte removal performance was low, and the blood process pressure was also high, demonstrating that this filter material is practically unsuitable.

Comparative Example 33

A nonwoven fabric consisting of PBT fiber and having a mass per unit area of 22 g/m$^2$, a thickness of 0.13 mm, a filling rate of 0.12, an average fiber diameter of 1.4 µm, and a formation index of 14.2 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducing the blood test by the same method as in Example 1, the leukocyte residual rate was $3.1 \times 10^{-3}$, and the blood process pressure was 13.5 kPa. Although the leukocyte removal performance was high, the blood process pressure was high, demonstrating that this filter material is practically unsuitable.

Comparative Example 34

A nonwoven fabric consisting of PBT fiber and having a mass per unit area of 22 g/m$^2$, a thickness of 0.13 mm, a filling rate of 0.12, an average fiber diameter of 1.6 µm, and a formation index of 16.5 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducing the blood test by the same method as in Example 1, the leukocyte residual rate was $11.2 \times 10^{-3}$, and the blood process pressure was 4.5 kPa. Although the blood process pressure was low, the leukocyte removal performance was low, demonstrating that this filter material is practically unsuitable.

Comparative Example 35

A nonwoven fabric consisting of PBT fiber and having a mass per unit area of 22 g/m$^2$, a thickness of 0.13 mm, a filling rate of 0.12, an average fiber diameter of 1.5 µm, and a formation index of 67.2 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $36.5 \times 10^{-3}$, and the blood process pressure was 3.3 kPa. Although the blood process pressure was low, the leukocyte removal performance was low, demonstrating that this filter material is practically unsuitable.

Comparative Example 36

A nonwoven fabric consisting of PBT fiber and having a mass per unit area of 22 g/m$^2$, a thickness of 0.13 mm, a filling rate of 0.12, an average fiber diameter of 0.9 µm, and a formation index of 62.9 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $16.1 \times 10^{-3}$, and the blood process pressure was 7.0 kPa. Although the blood process pressure was low, the leukocyte removal performance was low, demonstrating that this filter material is practically unsuitable.

Comparative Example 37

A nonwoven fabric consisting of PBT fiber and having a mass per unit area of 22 g/m$^2$, a thickness of 0.13 mm, a filling rate of 0.12, an average fiber diameter of 0.9 µm, and a formation index of 52.0 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducing the blood test by the same method as in Example 1, the leukocyte residual rate was $13.4 \times 10^{-3}$, and the blood process pressure was 10.3 kPa. The leukocyte removal performance was low, and the blood process pressure was also high, demonstrating that this filter material is practically unsuitable.

Comparative Example 38

A nonwoven fabric consisting of PBT fiber and having a mass per unit area of 22 g/m$^2$, a thickness of 0.13 mm, a filling rate of 0.12, an average fiber diameter of 1.5 μm, and a formation index of 67.2 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $39.6 \times 10^{-3}$, and the blood process pressure was 2.9 kPa. Although the blood process pressure was low, the leukocyte removal performance was low, demonstrating that this filter material is practically unsuitable.

Comparative Example 39

A nonwoven fabric consisting of PBT fiber and having a mass per unit area of 22 g/m², a thickness of 0.13 mm, a filling rate of 0.12, an average fiber diameter of 0.9 μm, and a formation index of 62.9 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $19.1 \times 10^{-3}$, and the blood process pressure was 6.4 kPa. Although the blood process pressure was low, the leukocyte removal performance was low, demonstrating that this filter material is practically unsuitable.

Comparative Example 40

A nonwoven fabric consisting of PBT fiber and having a mass per unit area of 22 g/m², a thickness of 0.13 mm, a filling rate of 0.12, an average fiber diameter of 0.9 μm, and a formation index of 52.0 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $14.7 \times 10^{-3}$, and the blood process pressure was 9.9 kPa. Although the blood process pressure was low, the leukocyte removal performance was low, demonstrating that this filter material is practically unsuitable.

Comparative Example 41

A nonwoven fabric consisting of PBT fiber and having a mass per unit area of 22 g/m², a thickness of 0.13 mm, a filling rate of 0.12, an average fiber diameter of 1.4 μm, and a formation index of 69.1 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $21.5 \times 10^{-3}$, and the blood process pressure was 4.4 kPa. Although the blood process pressure was low, the leukocyte removal performance was low, demonstrating that this filter material is practically unsuitable.

Comparative Example 42

A nonwoven fabric consisting of PBT fiber and having a mass per unit area of 22 g/m², a thickness of 0.12 mm, a filling rate of 0.14, an average fiber diameter of 1.5 μm, and a formation index of 69.2 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100. dyn/cm. The nonwoven fabric after the polymer coating treatment was used as a leukocyte removal filter material. As a result of conducting the blood test by the same method as in Example 1, the leukocyte residual rate was $23.5 \times 10^{-3}$, and the blood process pressure was 5.2 kPa. Although the blood process pressure was low, the leukocyte removal performance was low, demonstrating that this filter material is practically unsuitable.

Comparative Example 43

A nonwoven fabric consisting of PBT fiber and having a mass per unit area of 22 g/m², a thickness of 0.16 mm, a filling rate of 0.10, an average fiber diameter of 1.0 μm, and a formation index of 69.3 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $26.4 \times 10^{-3}$, and the blood process pressure was 2.9 kPa. Although the blood process pressure was low, the leukocyte removal performance was low, demonstrating that this filter material is practically unsuitable.

Comparative Example 44

A nonwoven fabric consisting of PBT fiber and having a mass per unit area of 22 g/m², a thickness of 0.10 mm, a filling rate of 0.17, an average fiber diameter of 0.9 μm, and a formation index of 52.0 was used. The nonwoven fabric was prepared by a method of subjecting a fiber assembly after spinning to heat treatment in the same way as in Example 1. The same polymer coating treatment as in Example 1 was carried out for the nonwoven fabric. The CWST value after the polymer coating treatment was 100 dyn/cm. The nonwoven fabric after the polymer coating treatment was used as a leukocyte removal filter material. As a result of conducting the blood test by the same method as in Example 1, the leukocyte residual rate was $11.2 \times 10^{-3}$, and the blood process pressure was 21.3 kPa. The leukocyte removal performance was low, and the blood process pressure was also high, demonstrating that this filter material is practically unsuitable.

Comparative Example 45

A nonwoven fabric consisting of PBT fiber and having a mass per unit area of 22 g/m², a thickness of 0.13 mm, a filling rate of 0.12, an average fiber diameter of 1.4 µm, and a formation index of 69.1 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $23.5 \times 10^{-3}$, and the blood process pressure was 4.0 kPa. Although the blood process pressure was low, the leukocyte removal performance was low, demonstrating that this filter material is practically unsuitable.

Comparative Example 46

A nonwoven fabric consisting of PBT fiber and having a mass per unit area of 22 g/m$^2$, a thickness of 0.12 mm, a filling rate of 0.14, an average fiber diameter of 1.5 µm, and a formation index of 69.2 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $26.0 \times 10^{-3}$, and the blood process pressure was 4.8 kPa. Although the blood process pressure was low, the leukocyte removal performance was low, demonstrating that this filter material is practically unsuitable.

Comparative Example 47

A nonwoven fabric consisting of PBT fiber and having a mass per unit area of 22 g/m$^2$, a thickness of 0.16 mm, a filling rate of 0.10, an average fiber diameter of 1.0 µm, and a formation index of 69.3 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $29.0 \times 10^{-3}$, and the blood process pressure was 2.7 kPa. Although the blood process pressure was low, the leukocyte removal performance was low, demonstrating that this filter material is practically unsuitable.

Comparative Example 48

A nonwoven fabric consisting of PBT fiber and having a mass per unit area of 22 g/m$^2$, a thickness of 0.10 mm, a filling rate of 0.17, an average fiber diameter of 0.9 µm, and a formation index of 52.0 was used. The nonwoven fabric was prepared by a method of subjecting a fiber assembly after spinning to heat treatment in the same way as in Example 1. The polymer coating treatment of the nonwoven fabric was not carried out. The CWST value was 51 dyn/cm. The nonwoven fabric without the polymer coating treatment described above was used as a filter material. As a result of conducting the blood test by the same method as in Example 1, the leukocyte residual rate was $14.0 \times 10^{-3}$, and the blood process pressure was 19.3 kPa. The leukocyte removal performance was low, and the blood process pressure was also high, demonstrating that this filter material is practically unsuitable.

TABLE 1

|  | Example 1 | Example 2 | Example 3 | Example 4 | Example 5 | Example 6 | Example 7 | Example 8 |
|---|---|---|---|---|---|---|---|---|
| Nonwoven fabric filter material | PBT | PBT | PBT | PBT | PBT | PBT | PBT | PBT |
| Mass per unit area (g/m$^2$) | 22 | 23 | 22 | 23 | 22 | 23 | 22 | 23 |
| Thickness (mm) | 0.13 | 0.13 | 0.13 | 0.13 | 0.13 | 0.13 | 0.13 | 0.13 |
| Filling rate | 0.12 | 0.13 | 0.12 | 0.13 | 0.12 | 0.13 | 0.12 | 0.13 |
| Formation index (Z) | 18.0 | 68.9 | 17.1 | 67.5 | 18.0 | 68.9 | 17.1 | 67.5 |
| Average fiber diameter (X) | 1.0 | 1.0 | 1.4 | 1.4 | 1.0 | 1.0 | 1.4 | 1.4 |
| Specific surface area (Y) | 1.66 | 1.50 | 1.20 | 1.10 | 1.67 | 1.54 | 1.24 | 1.11 |
| 1.75 − 0.65*X value | 1.10 | 1.10 | 0.84 | 0.84 | 1.10 | 1.10 | 0.84 | 0.84 |
| Formation index/specific surface area (Z/Y) | 11.3 | 45.9 | 14.3 | 61.4 | 11.0 | 44.7 | 13.8 | 60.6 |
| Mean flow pore size (W) | 1.2 | 5.6 | 3.9 | 8.1 | 2.0 | 5.9 | 4.4 | 9.3 |
| Presence or absence of coating treatment | Present | Present | Present | Present | Absent | Absent | Absent | Absent |
| Leukocyte residual rate (×10$^{-3}$) | 0.3 | 7.1 | 4.4 | 9.2 | 0.5 | 3.2 | 2.3 | 6.2 |
| Process pressure (kPa) | 9.5 | 5.2 | 7.3 | 3.0 | 8.4 | 4.7 | 6.8 | 2.7 |

TABLE 2

|  | Example 9 | Example 10 | Example 11 | Example 12 | Example 13 | Example 14 | Example 15 | Example 16 | Example 17 | Example 18 |
|---|---|---|---|---|---|---|---|---|---|---|
| Nonwoven fabric filter material | PBT | PBT | PBT | PBT | PBT | PBT | PBT | PBT | PBT | PBT |
| Mass per unit area (g/m$^2$) | 22 | 23 | 22 | 23 | 22 | 23 | 22 | 22 | 23 | 22 |
| Thickness (mm) | 0.13 | 0.13 | 0.13 | 0.13 | 0.13 | 0.13 | 0.13 | 0.13 | 0.13 | 0.13 |
| Filling rate | 0.12 | 0.13 | 0.12 | 0.13 | 0.12 | 0.13 | 0.12 | 0.12 | 0.13 | 0.12 |
| Formation index (Z) | 38.0 | 55.0 | 38.0 | 55.0 | 16.3 | 65.1 | 15.1 | 16.3 | 65.1 | 15.1 |

TABLE 2-continued

|  | Example 9 | Example 10 | Example 11 | Example 12 | Example 13 | Example 14 | Example 15 | Example 16 | Example 17 | Example 18 |
|---|---|---|---|---|---|---|---|---|---|---|
| Average fiber diameter (X) | 1.4 | 1.3 | 1.4 | 1.3 | 0.9 | 1.5 | 1.0 | 0.9 | 1.5 | 1.0 |
| Specific surface area (Y) | 1.41 | 1.48 | 1.45 | 1.53 | 2.68 | 0.97 | 1.96 | 2.72 | 1.00 | 2.01 |
| 1.75 − 0.65*X value | 0.84 | 0.91 | 0.84 | 0.91 | 1.17 | 0.78 | 1.10 | 1.17 | 0.78 | 1.10 |
| Formation index/specific surface area (Z/Y) | 27.0 | 37.2 | 26.2 | 35.9 | 6.1 | 67.1 | 7.7 | 6.0 | 65.1 | 7.5 |
| Mean flow pore size (W) | 6.1 | 4.7 | 6.4 | 5.0 | 1.0 | 7.9 | 0.8 | 1.7 | 8.4 | 0.9 |
| Presence or absence of coating treatment | Present | Present | Absent | Absent | Present | Present | Present | Absent | Absent | Absent |
| Leukocyte residual rate (×10⁻³) | 2.7 | 5.0 | 3.2 | 5.4 | 0.2 | 9.3 | 0.1 | 0.3 | 9.7 | 0.3 |
| Process pressure (kPa) | 7.9 | 6.6 | 7.2 | 5.8 | 9.6 | 3.2 | 9.9 | 8.3 | 5.8 | 9.7 |

TABLE 3

|  | Comp. Example 1 | Comp. Example 2 | Comp. Example 3 | Com. Example 4 | Comp. Example 5 | Comp. Example 6 | Comp. Example 7 | Comp. Example 8 |
|---|---|---|---|---|---|---|---|---|
| Nonwoven fabric filter material | PET | PET | PET | PET | PET | PET | PET | PET |
| Mass per unit area (g/m²) | 22 | 23 | 22 | 23 | 22 | 23 | 22 | 23 |
| Thickness (mm) | 0.13 | 0.13 | 0.13 | 0.13 | 0.13 | 0.13 | 0.13 | 0.13 |
| Filling rate | 0.12 | 0.13 | 0.12 | 0.13 | 0.12 | 0.13 | 0.12 | 0.13 |
| Formation index (Z) | 17.0 | 68.1 | 16.6 | 67.7 | 17.0 | 68.1 | 16.6 | 67.7 |
| Average fiber diameter (X) | 1.0 | 1.0 | 1.4 | 1.4 | 1.0 | 1.0 | 1.4 | 1.4 |
| Specific surface area (Y) | 1.30 | 0.95 | 1.00 | 0.73 | 1.26 | 0.97 | 0.97 | 0.77 |
| 1.75 − 0.65*X value | 1.10 | 1.10 | 0.84 | 0.84 | 1.10 | 1.10 | 0.84 | 0.84 |
| Formation index/specific surface area (Z/Y) | 13.1 | 71.7 | 16.6 | 92.7 | 13.5 | 70.2 | 17.2 | 87.9 |
| Mean flow pore size (W) | 1.1 | 5.8 | 3.5 | 9.3 | 0.9 | 6.1 | 3.9 | 10.1 |
| Presence or absence of coating treatment | Present | Present | Present | Present | Absent | Absent | Absent | Absent |
| Leukocyte residual rate (×10⁻³) | 0.6 | 21.2 | 4.8 | 48.9 | 1.0 | 27.3 | 6.5 | 57.3 |
| Process pressure (kPa) | 22.0 | 8.8 | 17.7 | 3.2 | 18.5 | 7.7 | 17.4 | 2.4 |

TABLE 4

|  | Comp. Example 9 | Comp. Example 10 | Comp. Example 11 | Comp. Example 12 | Comp. Example 13 | Comp. Example 14 | Comp. Example 15 | Comp. Example 16 |
|---|---|---|---|---|---|---|---|---|
| Nonwoven fabric filter material | PET | PET | PET | PET | PET | PET | PET | PET |
| Mass per unit area (g/m²) | 22 | 23 | 22 | 23 | 22 | 23 | 22 | 22 |
| Thickness (mm) | 0.13 | 0.13 | 0.13 | 0.13 | 0.13 | 0.13 | 0.13 | 0.13 |
| Filling rate | 0.12 | 0.13 | 0.12 | 0.13 | 0.12 | 0.13 | 0.12 | 0.12 |
| Formation index (Z) | 38.0 | 55.0 | 38.0 | 55.0 | 16.0 | 64.7 | 15.2 | 16.0 |
| Average fiber diameter (X) | 1.4 | 1.3 | 1.4 | 1.3 | 0.9 | 1.5 | 1.0 | 0.9 |
| Specific surface area (Y) | 0.92 | 0.82 | 0.95 | 0.85 | 1.48 | 0.67 | 1.33 | 1.52 |
| 1.75 − 0.65*X value | 0.84 | 0.91 | 0.84 | 0.91 | 1.17 | 0.78 | 1.10 | 1.17 |
| Formation index/specific surface area (Z/Y) | 41.3 | 67.1 | 40.0 | 64.7 | 10.8 | 96.6 | 11.4 | 10.5 |
| Mean flow pore size (W) | 7.2 | 5.9 | 7.5 | 6.8 | 1.3 | 12.1 | 1.0 | 1.5 |
| Presence or absence of coating treatment | Present | Present | Absent | Absent | Present | Present | Present | Absent |
| Leukocyte residual rate (×10⁻³) | 10.3 | 18.1 | 11.4 | 23.2 | 0.4 | 78.3 | 0.3 | 0.6 |
| Process pressure (kPa) | 5.1 | 6.4 | 4.7 | 6.1 | 24.1 | 1.9 | 29.3 | 22.1 |

TABLE 5

|  | Comp. Example 17 | Comp. Example 18 |
|---|---|---|
| Nonwoven fabric filter material | PET | PET |
| Mass per unit area (g/m²) | 23 | 22 |
| Thickness (mm) | 0.13 | 0.13 |
| Filling rate | 0.13 | 0.12 |
| Formation index (Z) | 64.7 | 15.2 |
| Average fiber diameter (X) | 1.5 | 1.0 |
| Specific surface area (Y) | 0.68 | 1.35 |
| 1.75 − 0.65*X value | 0.78 | 1.10 |

TABLE 5-continued

|  | Comp. Example 17 | Comp. Example 18 |
|---|---|---|
| Formation index/specific surface area (Z/Y) | 95.1 | 11.3 |
| Mean flow pore size (W) | 12.7 | 1.2 |
| Presence or absence of coating treatment | Absent | Absent |
| Leukocyte residual rate (×10$^{-3}$) | 81.4 | 0.5 |
| Process pressure (kPa) | 1.8 | 27.9 |

TABLE 6

|  | Comp. Example 19 | Comp. Example 20 | Comp. Example 21 | Comp. Example 22 | Comp. Example 23 | Comp. Example 24 | Comp. Example 25 | Comp. Example 26 |
|---|---|---|---|---|---|---|---|---|
| Nonwoven fabric filter material | PBT | PBT | PBT | PBT | PBT | PBT | PBT | PBT |
| Mass per unit area (g/m$^2$) | 22 | 22 | 22 | 22 | 22 | 22 | 22 | 22 |
| Thickness (mm) | 0.13 | 0.13 | 0.13 | 0.13 | 0.13 | 0.13 | 0.13 | 0.13 |
| Filling rate | 0.12 | 0.12 | 0.12 | 0.12 | 0.12 | 0.12 | 0.12 | 0.12 |
| Formation index (Z) | 16.1 | 66.1 | 13.5 | 71.5 | 16.1 | 66.1 | 13.5 | 71.5 |
| Average fiber diameter (X) | 0.8 | 1.6 | 1.0 | 1.4 | 0.8 | 1.6 | 1.0 | 1.4 |
| Specific surface area (Y) | 2.07 | 0.98 | 1.54 | 0.81 | 2.12 | 1.04 | 1.80 | 0.83 |
| 1.75 − 0.65*X | 1.23 | 0.71 | 1.10 | 0.84 | 1.23 | 0.71 | 1.10 | 0.84 |
| Formation index/specific surface area (Z/Y) | 7.8 | 67.4 | 8.8 | 88.3 | 7.6 | 63.6 | 7.5 | 86.1 |
| Mean flow pore size (W) | 0.7 | 9.2 | 0.8 | 8.4 | 0.8 | 9.6 | 0.9 | 8.7 |
| Presence or absence of coating treatment | Present | Present | Present | Present | Absent | Absent | Absent | Absent |
| Leukocyte residual rate (×10$^{-3}$) | 0.7 | 19.3 | 1.3 | 28.5 | 1.2 | 24.0 | 4.2 | 31.0 |
| Process pressure (kPa) | 43.0 | 2.7 | 20.1 | 4.3 | 39.0 | 2.2 | 15.0 | 3.5 |

TABLE 7

|  | Comp. Example 27 | Comp. Example 28 | Comp. Example 29 | Comp. Example 30 | Comp. Example 31 | Comp. Example 32 | Comp. Example 33 | Comp. Example 34 |
|---|---|---|---|---|---|---|---|---|
| Nonwoven fabric filter material | PBT | PBT | PBT | PBT | PBT | PBT | PBT | PBT |
| Mass per unit area (g/m$^2$) | 22 | 22 | 22 | 22 | 22 | 22 | 22 | 22 |
| Thickness (mm) | 0.13 | 0.13 | 0.13 | 0.13 | 0.13 | 0.13 | 0.13 | 0.13 |
| Filling rate | 0.12 | 0.12 | 0.12 | 0.12 | 0.12 | 0.12 | 0.12 | 0.12 |
| Formation index (Z) | 71.3 | 67.3 | 13.5 | 15.9 | 70.8 | 68.9 | 14.2 | 16.5 |
| Average fiber diameter (X) | 1.0 | 0.8 | 1.4 | 1.6 | 1.0 | 0.8 | 1.4 | 1.6 |
| Specific surface area (Y) | 1.05 | 1.19 | 1.24 | 1.06 | 1.08 | 1.22 | 1.36 | 1.10 |
| 1.75 − 0.65*X | 1.1 | 1.23 | 0.84 | 0.71 | 1.1 | 1.23 | 0.84 | 0.71 |
| Formation index/specific surface area (Z/Y) | 67.9 | 56.6 | 10.9 | 15.0 | 65.6 | 56.5 | 10.4 | 15.0 |
| Mean flow pore size (W) | 6.1 | 4.2 | 3.2 | 6.3 | 6.5 | 4.4 | 3.5 | 5.7 |
| Presence or absence of coating treatment | Present | Present | Present | Present | Absent | Absent | Absent | Absent |
| Leukocyte residual rate (×10$^{-3}$) | 18.4 | 11.3 | 2.8 | 10.1 | 19.7 | 12.3 | 3.1 | 11.2 |
| Process pressure (kPa) | 4.4 | 10.9 | 15.1 | 4.9 | 3.9 | 10.2 | 13.5 | 4.5 |

TABLE 8

|  | Comp. Example 35 | Comp. Example 36 | Comp. Example 37 | Comp. Example 38 | Comp. Example 39 | Comp. Example 40 |
|---|---|---|---|---|---|---|
| Nonwoven fabric filter material | PBT | PBT | PBT | PBT | PBT | PBT |
| Mass per unit area (g/m$^2$) | 22 | 22 | 22 | 22 | 22 | 22 |
| Thickness (mm) | 0.13 | 0.13 | 0.13 | 0.13 | 0.13 | 0.13 |
| Filling rate | 0.12 | 0.12 | 0.12 | 0.12 | 0.12 | 0.12 |
| Formation index (Z) | 69.2 | 68.9 | 52.0 | 69.2 | 68.9 | 52.0 |
| Average fiber diameter (X) | 1.5 | 0.9 | 0.9 | 1.5 | 0.9 | 0.9 |
| Specific surface area (Y) | 0.76 | 1.06 | 1.15 | 0.77 | 1.08 | 1.16 |
| 1.75 − 0.65*X | 0.78 | 1.17 | 1.17 | 0.78 | 1.17 | 1.17 |
| Formation index/specific surface area (Z/Y) | 89.9 | 62.6 | 45.2 | 89.8 | 63.8 | 44.8 |

TABLE 8-continued

|  | Comp. Example 35 | Comp. Example 36 | Comp. Example 37 | Comp. Example 38 | Comp. Example 39 | Comp. Example 40 |
|---|---|---|---|---|---|---|
| Mean flow pore size (W) | 8.9 | 5.3 | 4.4 | 9.1 | 5.5 | 4.6 |
| Presence or absence of coating treatment | Present | Present | Present | Absent | Absent | Absent |
| Leukocyte residual rate ($\times 10^{-3}$) | 36.5 | 16.1 | 13.4 | 39.6 | 19.1 | 14.7 |
| Process pressure (kPa) | 3.3 | 7.0 | 10.3 | 2.9 | 6.4 | 9.9 |

TABLE 9

|  | Comp. Example 41 | Comp. Example 42 | Comp. Example 43 | Comp. Example 44 | Comp. Example 45 | Comp. Example 46 | Comp. Example 47 | Comp. Example 48 |
|---|---|---|---|---|---|---|---|---|
| Nonwoven fabric filter material | PBT | PBT | PBT | PBT | PBT | PBT | PBT | PBT |
| Mass per unit area (g/m$^2$) | 22 | 22 | 22 | 22 | 22 | 22 | 22 | 22 |
| Thickness (mm) | 0.13 | 0.12 | 0.16 | 0.10 | 0.13 | 0.12 | 0.16 | 0.10 |
| Filling rate | 0.12 | 0.14 | 0.10 | 0.17 | 0.12 | 0.14 | 0.10 | 0.17 |
| Formation index (Z) | 69.1 | 69.2 | 69.3 | 52.0 | 69.1 | 69.2 | 69.3 | 52.0 |
| Average fiber diameter (X) | 1.4 | 1.5 | 1.0 | 0.9 | 1.4 | 1.5 | 1.0 | 0.9 |
| Specific surface area (Y) | 0.82 | 0.75 | 1.08 | 1.06 | 0.83 | 0.76 | 1.09 | 1.08 |
| 1.75 − 0.65*X | 0.84 | 0.78 | 1.10 | 1.17 | 0.84 | 0.78 | 1.10 | 1.17 |
| Formation index/specific surface area (Z/Y) | 84.3 | 92.2 | 64.1 | 49.1 | 83.3 | 91.1 | 64.1 | 48.1 |
| Mean flow pore size (W) | 7.9 | 7.7 | 11.1 | 0.8 | 8.0 | 7.8 | 12.1 | 0.9 |
| Presence or absence of coating treatment | Present | Present | Present | Present | Absent | Absent | Absent | Absent |
| Leukocyte residual rate ($\times 10^{-3}$) | 21.5 | 23.5 | 26.4 | 11.2 | 23.5 | 26.0 | 29.0 | 14.0 |
| Process pressure (kPa) | 4.4 | 5.2 | 2.9 | 21.3 | 4.0 | 4.8 | 2.7 | 19.3 |

As shown in Tables 1 to 9, it was found from the results of Examples 1 to 18 and Comparative Examples 1 to 48 that high leukocyte removal performance and a low blood process pressure, i.e., good flowability, can be attained by using the PBT nonwoven fabric and controlling the formation index and the average fiber diameter in the optimum ranges. It was also suggested that it is important for the balance between the high leukocyte removal performance and the low blood process pressure to set the specific surface area to be high by using the PBT nonwoven fabric, while suppressing excessive reduction in average fiber diameter. Furthermore, if the mean flow pore size of the nonwoven fabric was 1 μm or smaller, a tendency that flowability was reduced was observed. In addition, further improvement in leukocyte removal performance and the effect of lowering a process pressure were confirmed by carrying out the polymer coating treatment, suggesting that it contributes to improvement in performance balance.

INDUSTRIAL APPLICABILITY

In the leukocyte removal method of the present invention compared with the conventional method, the leukocyte removal performance can be enhanced, and the processing time can be shortened without clogging, by using a polybutylene terephthalate nonwoven fabric and using a leukocyte removal filter material with the formation index and the fiber diameter controlled in the optimum ranges. It is very effective to use the leukocyte removal filter material and the leukocyte removal method of the present invention for capturing leukocytes contained in blood.

REFERENCE SIGNS LIST

1: Container, 3: First port (liquid inlet/outlet), 4: Second port (liquid inlet/outlet), 5: Leukocyte removal filter material, 7: Space on the first port side, 8: Space on the second port side, and 10: Leukocyte removal filter.

The invention claimed is:

1. A filter material comprising a nonwoven fabric having polybutylene terephthalate fiber, wherein
   an average fiber diameter of the nonwoven fabric is greater than 1.1 and less than 1.5 μm,
   a formation index corresponding to a thickness of 0.3 mm of the nonwoven fabric is 15 to 70, and
   which satisfies the following relational expression (1):

$$1.66 > Y \leq -0.65 \times X + 2.30 \quad (1)$$

where X is average fiber diameter of the nonwoven fabric (in μm), and Y is specific surface area of the nonwoven fabric Y (in m$^2$/g).

2. The filter material according to claim 1, wherein the nonwoven fabric is a nonwoven fabric obtained by a melt blowing method.

3. The filter material according to claim 1, wherein an area shrinkage percentage when the nonwoven fabric is heat-treated at 115° C. for 240 minutes is 10% or less.

4. The filter material according to claim 1 or 2, wherein a critical wetting surface tension of the nonwoven fabric is 50 dyn/cm or larger.

5. The filter material according to claim 1 or 2, wherein a bulk density of the nonwoven fabric is 0.05 to 0.30 g/cm$^3$.

6. The filter material according to claim 1 or 2, wherein an airflow resistance of the nonwoven fabric is 25 Pa·s·m/g or larger and 100 Pa·s·m/g or smaller.

7. The filter material according to claim 1 or 2, wherein a peripheral surface portion of the nonwoven fabric has a nonionic group and a basic nitrogen-containing functional group, and a molar ratio of the nonionic group to the basic nitrogen-containing functional group is 20.0:1 to 50.0:1.

8. The filter material according to claim 1 or 2, wherein when a specific surface area of the nonwoven fabric is Y and a formation index corresponding to a thickness of 0.3 mm of the nonwoven fabric is Z, Y and Z satisfy the following relational expression (2):

$$6.2 \leq Z/Y \leq 66 \quad (2).$$

9. The filter material according to claim 8, wherein when a mean flow pore size of the nonwoven fabric in μm is W, W satisfies the following relational expression (3):

$$1.0 \leq W \leq 8.0 \quad (3).$$

10. The filter material according to claim 9, wherein when a whole blood product is allowed to pass through the filter material at a flow rate of 1.2 mL/min, a leukocyte residual rate is $10.0 \times 10^{-3}$ or less, and a process pressure is 20.0 kPa or smaller, the filter material having an effective filtration area of 1.3 cm² and a mass of 320 g/m².

11. The filter material according to claim 9 for removing leukocytes from a leukocyte-containing solution which is any of whole blood, a concentrated red cell solution, platelet-rich plasma, and platelet-poor plasma.

12. The filter material of claim 1 wherein the average fiber diameter of the nonwoven fabric is 1.3 to less than 1.5 μm.

13. A method for removing leukocytes from a leukocyte-containing solution, comprising allowing the leukocyte-containing solution to pass through the filter material according to claim 9.

14. The method according to claim 13, wherein the leukocyte-containing solution is any of whole blood, a concentrated red cell solution, platelet-rich plasma, and platelet-poor plasma.

15. The filter material according to claim 1 or 2, wherein when a whole blood product is allowed to pass through the filter material at a flow rate of 1.2 mL/min, a leukocyte residual rate is $10.0 \times 10^{-3}$ or less, and a process pressure is 20.0 kPa or smaller, the filter material having an effective filtration area of 1.3 cm² and a mass of 320 g/m².

* * * * *

UNITED STATES PATENT AND TRADEMARK OFFICE
CERTIFICATE OF CORRECTION

| | |
|---|---|
| PATENT NO. | : 11,213,776 B2 |
| APPLICATION NO. | : 15/103435 |
| DATED | : January 4, 2022 |
| INVENTOR(S) | : T. Uchimura et al. |

It is certified that error appears in the above-identified patent and that said Letters Patent is hereby corrected as shown below:

In the Claims

Column 48, Line 45 (Claim 1, Line 8) please change "$Y \leq$" to -- $Y \geq$ --
Column 48, Line 61 (Claim 6, Line 2) please change "Pas·" to -- Pa·s· --

Signed and Sealed this
Seventh Day of June, 2022

*Katherine Kelly Vidal*

Katherine Kelly Vidal
*Director of the United States Patent and Trademark Office*